US011759606B2

United States Patent
Sandquist et al.

(10) Patent No.: US 11,759,606 B2
(45) Date of Patent: Sep. 19, 2023

(54) EXTENDED INTRODUCER FOR LEFT RADIAL ACCESS

(71) Applicant: Medtronic Vascular, Inc., Santa Rosa, CA (US)

(72) Inventors: Kelsey Sandquist, Santa Rosa, CA (US); Suruchi Anand, Rohnert Park, CA (US); Dishuan Chu, Rohnert Park, CA (US); Todd Grodrian, Santa Rosa, CA (US); Kelsey K. Kam, Santa Rosa, CA (US); Venmathi Gunasekaran, Sunnyvale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 15/930,134

(22) Filed: May 12, 2020

(65) Prior Publication Data

US 2020/0360656 A1    Nov. 19, 2020

Related U.S. Application Data

(60) Provisional application No. 62/847,149, filed on May 13, 2019.

(51) Int. Cl.
  *A61M 25/00*  (2006.01)
  *A61M 25/06*  (2006.01)
  (Continued)

(52) U.S. Cl.
  CPC ...... *A61M 25/0068* (2013.01); *A61M 25/005* (2013.01); *A61M 25/0012* (2013.01);
  (Continued)

(58) Field of Classification Search
  CPC ........ A61G 13/124; A61M 2205/0266; A61M 2025/0188; A61M 25/0068;
  (Continued)

(56) References Cited

U.S. PATENT DOCUMENTS 5,454,785 A * 10/1995 Smith ................... A61M 29/02
  604/510
5,849,016 A * 12/1998 Suhr ................. A61M 25/0169
  600/585

(Continued)

OTHER PUBLICATIONS

"StandTall Device for Left Radial Access Procedures", Radux Devices, retrieved from https://www.raduxdevices.com/products/standtall-10cm-15cm, accessed on May 5, 2020, 7 pp.

*Primary Examiner* — Katherine H Schwiker
*Assistant Examiner* — Robert F Allen
(74) *Attorney, Agent, or Firm* — Shumaker & Sieffert, P.A.

(57) ABSTRACT

An introducer extension with an extended, gradually curved section outside of the body enables a clinician to use an access site positioned across the body of that patient. An optional flexible or extendable section of the introducer extension allows a clinician to customize the shape of the introducer extension to a particular patient or clinician preference. The introducer extension includes a tubular sidewall extending along a longitudinal axis from a proximal end of the introducer extension to a distal end of the introducer extension and defining a lumen extending along the longitudinal axis. The tubular sidewall is configured to define a curved configuration having at least one curve (Continued)

between the proximal end and the distal end. The distal end is configured to couple to an introducer sheath. The lumen is configured to allow passage of a medical device.

34 Claims, 15 Drawing Sheets

(51) Int. Cl.
*A61M 25/02* (2006.01)
*A61M 25/01* (2006.01)

(52) U.S. Cl.
CPC .... *A61M 25/0054* (2013.01); *A61M 25/0097* (2013.01); *A61M 25/02* (2013.01); *A61M 25/0662* (2013.01); *A61M 2025/0047* (2013.01); *A61M 2025/0188* (2013.01); *A61M 2025/0206* (2013.01); *A61M 2025/0213* (2013.01); *A61M 2205/0266* (2013.01)

(58) Field of Classification Search
CPC .......... A61M 25/0097; A61M 25/0662; A61M 25/0045; A61M 2025/0047; A61M 25/005; A61M 25/0054; A61M 25/0668; A61M 25/0012; A61M 25/02; A61M 2025/0213; A61M 2025/0206; A61M 25/0009; A61M 25/0041; A61M 25/0069; A61F 5/3723
See application file for complete search history.

(56) References Cited

U.S. PATENT DOCUMENTS

| | | |
|---|---|---|
| 2002/0198502 A1* | 12/2002 | Vohsing ............ A61M 25/0668 604/537 |
| 2016/0089295 A1* | 3/2016 | Panetta .................. A61G 15/12 128/845 |
| 2017/0095640 A1* | 4/2017 | Rogers .............. A61M 25/0662 |
| 2018/0015254 A1* | 1/2018 | Cragg ............... A61M 25/0013 |
| 2018/0264236 A1* | 9/2018 | Gordon .............. A61M 39/223 |
| 2018/0339132 A1* | 11/2018 | Brunetti .................. A61M 5/14 |
| 2019/0021640 A1* | 1/2019 | Burkholz ......... A61B 5/150343 |
| 2019/0290525 A1* | 9/2019 | Kwarteng ............. A61G 13/12 |
| 2019/0321590 A1* | 10/2019 | Burkholz .......... A61M 25/0905 |

* cited by examiner

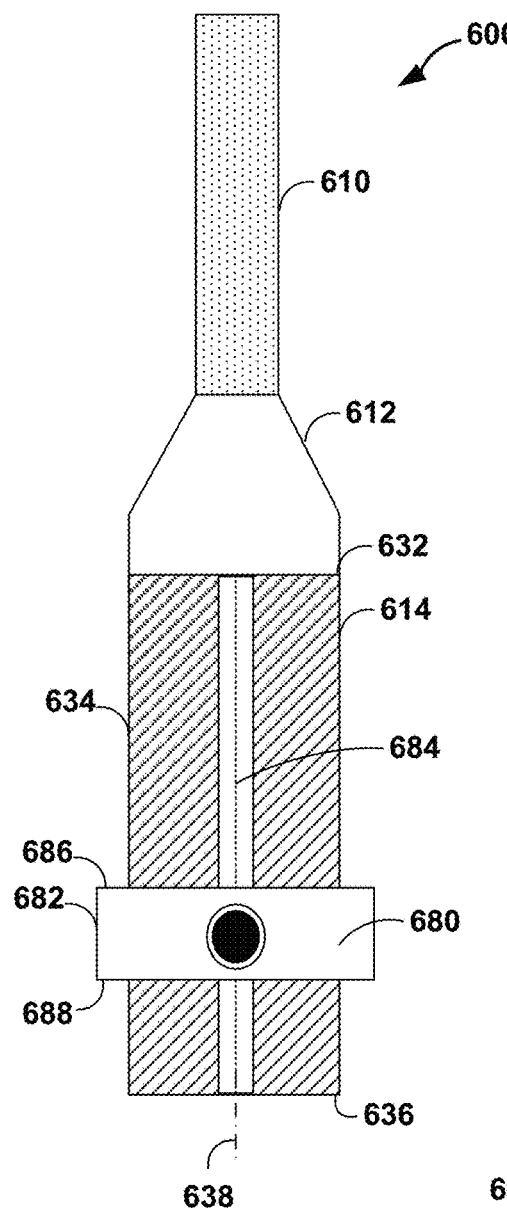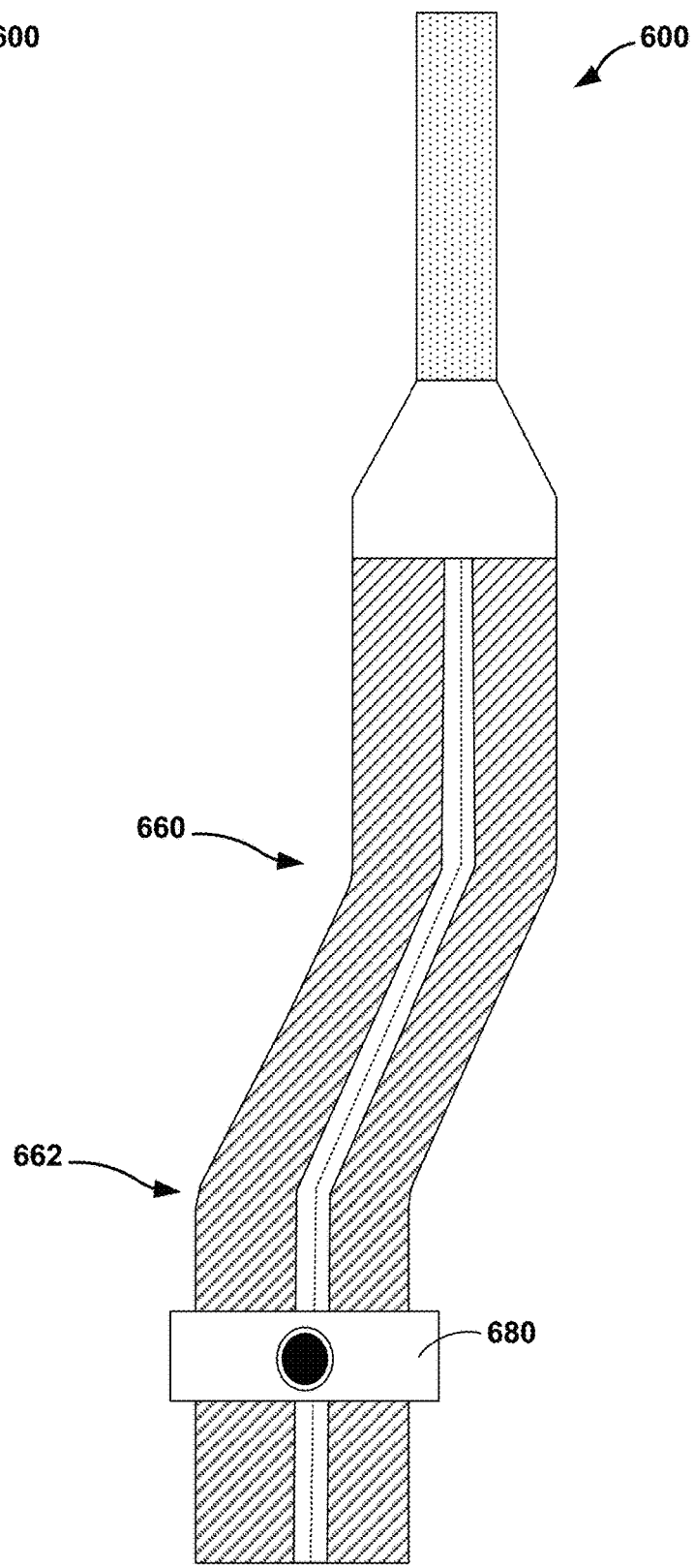
FIG. 6A
FIG. 6B

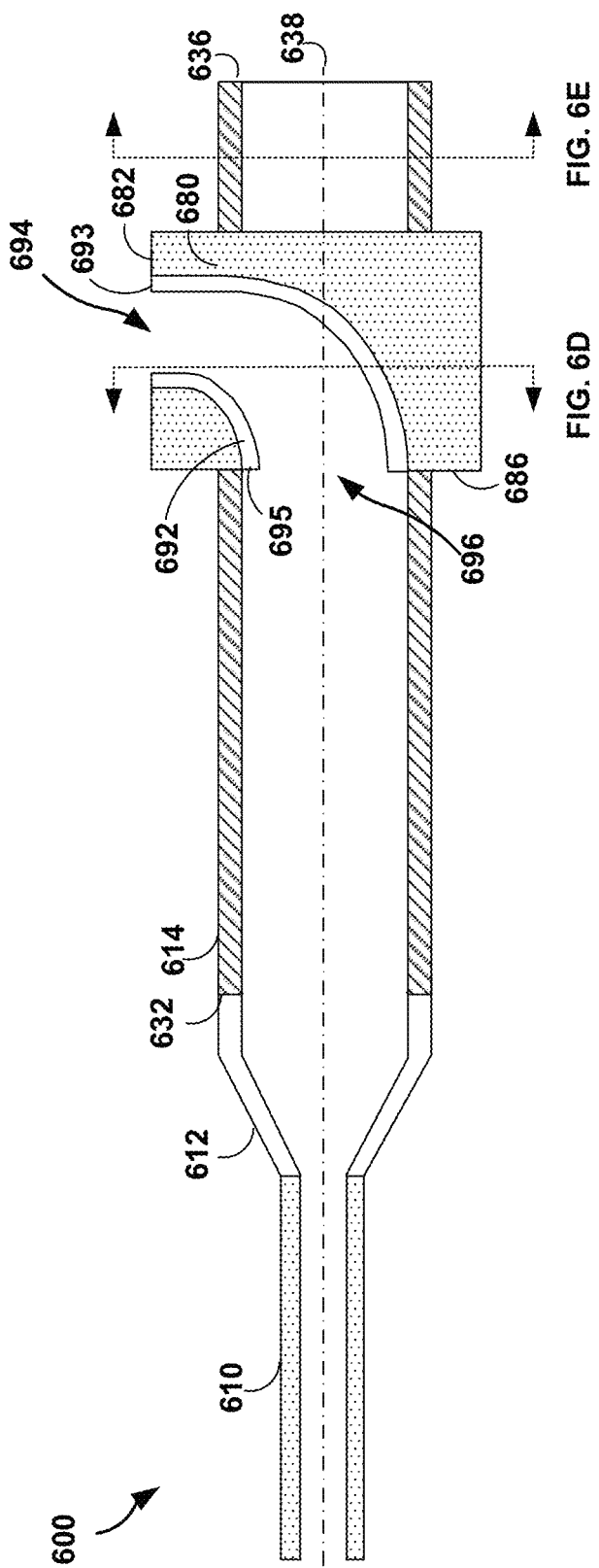

EXTENDED INTRODUCER FOR LEFT RADIAL ACCESS

This application claims the benefit of U.S. Provisional Application Ser. No. 62/847,149, entitled "EXTENDED INTRODUCER FOR LEFT RADIAL ACCESS," and filed on May 13, 2019, the entire content of which is incorporated herein by reference.

TECHNICAL FIELD

This disclosure relates to devices and techniques for radial access in percutaneous coronary intervention procedures.

BACKGROUND

Medical catheters may be advanced through an access site into vasculature of a patient to provide a lumen through which medical devices or therapeutic agents may be introduced to reach a treatment site. For example, the access site for percutaneous coronary intervention (PCI) procedures may include the radial artery or the femoral artery of a patient.

SUMMARY

The present disclosure describes devices and techniques to facilitate radial access in percutaneous coronary intervention (PCI) procedures. An introducer extension with an extended, gradually curved section outside of the body may enable a clinician to use an access site that is positioned across the body of that patient. For example, described devices and techniques may enable a clinician to access the left radial artery while positioned at the right side of the patient. The introducer extension may be configured to be customizable to a particular patient and clinician preferences. In this way, the introducer extension may combine benefits of a femoral artery approach with the benefits of a radial artery approach.

In some examples, an introducer extension may include a tubular sidewall extending along a longitudinal axis from a proximal end of the introducer extension to a distal end of the introducer extension and define a lumen extending along the longitudinal axis. The tubular sidewall may be configured to define a curved configuration having at least one curve between the proximal end and the distal end. The distal end may be configured to couple to an introducer sheath. The lumen may be configured to allow passage of a medical device.

In some examples, a medical assembly may include an introducer sheath extending along a longitudinal axis from a distal end of the introducer sheath to a proximal end of the introducer sheath; a hub extending along the longitudinal axis from a distal end of the hub to a proximal end of the hub; and an introducer extension including a tubular sidewall extending along a longitudinal axis from a proximal end of the introducer extension to a distal end of the introducer extension and defining a lumen extending along the longitudinal axis. A distal portion of the sheath may be configured to be inserted transdermally into vasculature of a patient. A distal end of the hub may be configured to couple to the proximal end of the introducer sheath. The distal end of the introducer extension may be configured to couple to the proximal end of the hub. The tubular sidewall may be configured to define a curved configuration having at least one curve between the proximal end of the introducer extension and the distal end of the introducer extension. The introducer sheath, the hub, and the introducer extension may define a common lumen configured to allow passage of a medical device therethrough.

In some examples, a method of forming an introducer extension may include forming a tubular sidewall extending along a longitudinal axis from a proximal end of the introducer extension to a distal end of the introducer extension and defining a lumen extending along the longitudinal axis. The tubular sidewall may be configured to define a curved configuration having at least one curve between the proximal end and the distal end. The distal end may be configured to couple to an introducer sheath. The lumen may be configured to allow passage of a medical device. The method also may include shaping the tubular sidewall to define the curved configuration.

In some examples, a method of using a medical assembly may include introducing a distal portion of an introducer sheath into vasculature of a patient. The introducer sheath may extend along a longitudinal axis from the distal end of the introducer sheath to a proximal end of the introducer sheath. The proximal end of the introducer sheath may be coupled to a distal end of a hub extending from the distal end of the hub to a proximal end of the hub. The method also may include mechanically coupling the proximal end of the hub to a distal end of an introducer extension including a tubular sidewall extending along the longitudinal axis from the proximal end of the introducer extension to a distal end of the introducer extension. The tubular sidewall may be configured to define a curved configuration having at least one curve between the proximal end of the introducer extension and the distal end of the introducer extension. The introducer sheath, the hub, and the introducer extension may define a common lumen. The method also may include shaping the tubular sidewall into the curved configuration, and introducing a medical device through the common lumen into vasculature of the patient.

The details of one or more examples are set forth in the accompanying drawings and the description below. Other features, objects, and advantages will be apparent from the description and drawings, and from the claims.

BRIEF DESCRIPTION OF DRAWINGS

FIGS. 6A-6F are conceptual diagrams illustrating an example medical assembly that includes an introducer extension including a moveable port configured to slide along the length of introducer extension.

DETAILED DESCRIPTION

Figure 1:
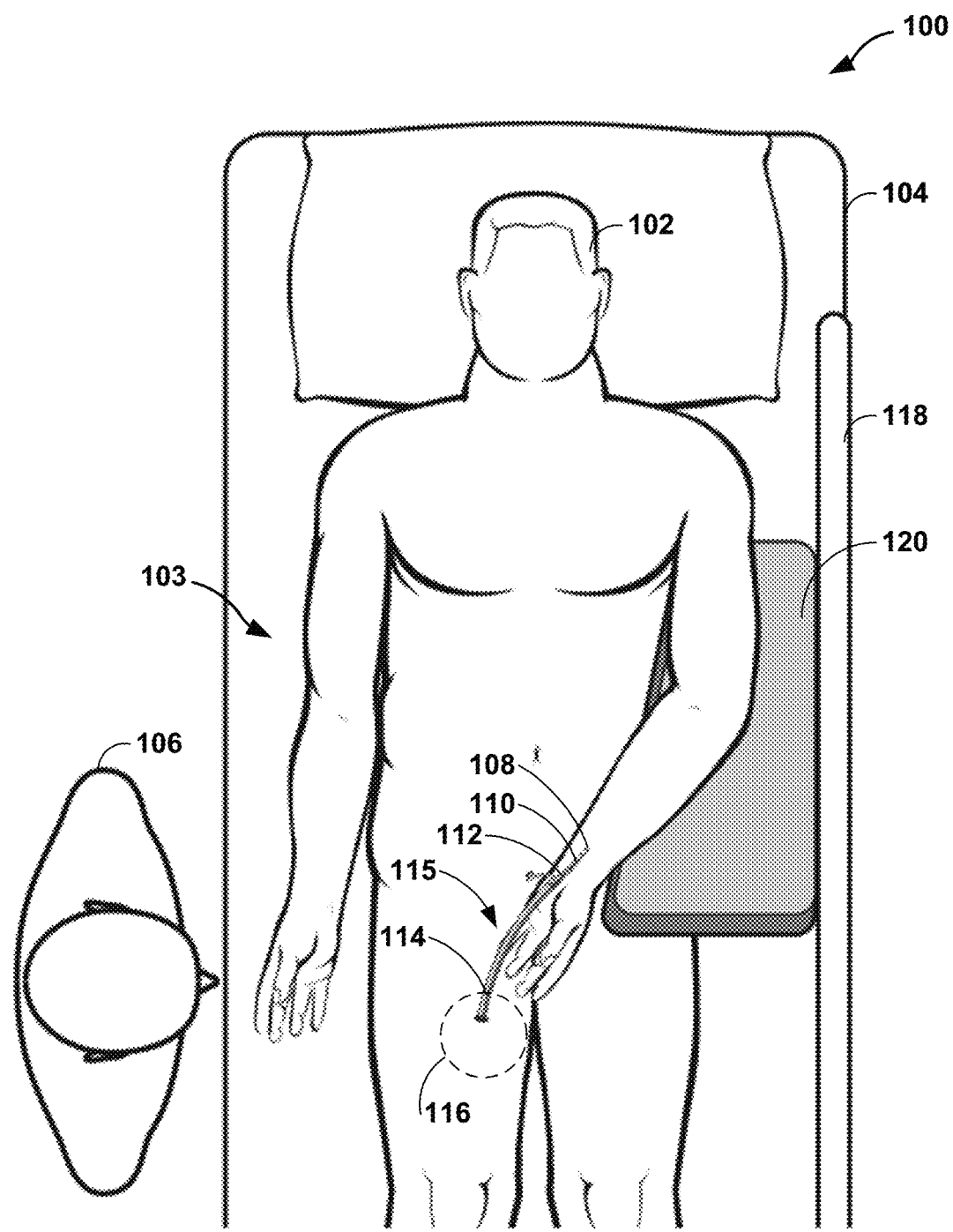
FIG. 1 is a schematic and conceptual diagram illustrating an example medical assembly including an introducer extension.

The present disclosure describes devices and techniques to improve percutaneous coronary intervention (PCI) procedures by allowing a clinician to control an effective arterial access site using a introducer extension. An introducer extension may include an extended, gradually curved section configured to be positioned outside of the body that enables a clinician to use an arterial access site ("access") that is positioned across the body of that patient, such as a left radial access. In some examples, the introducer extension may include at least one of a fixed curve, a flexible section, or an extendable section positioned outside of vasculature of the patient. The fixed curve may be shaped to correspond to the body shape of the patient, to better match the clinician's preferred position, and/or to accommodate catheterization lab space constraints. The flexible and/or extendable sections may enable a clinician to shape the introducer to better correspond to the size and body type of the patient, to better match the clinician's preferred position, and/or to accommodate catheterization lab space constraints.

In some examples, the introducer extension may enable a clinician to access the left radial artery while positioned at the right side of the patient. Left radial access may include several benefits over femoral access and right radial access. Compared to femoral access, radial access may present fewer bleeding risks, faster recovery, and lower costs. For example, patent hemostasis of a radial access may be achieved more quickly compared to a femoral access due to physiological factors such as the size of the artery and the relative ease with which pressure may be controllably applied to a radial access site. Additionally, the patient may be ambulatory more quickly after a radial access compared to a femoral access, which may reduce costs of post-operative care, reduce post-operative complications such as blood clots, and improve patient comfort.

Compared to right radial access, a left radial access may present less vessel tortuosity, thereby easing navigation of a catheter to the treatment site. Additionally, left radial access may provide different pathway through vasculature to a target treatment site, such as a coronary artery. In this way, the left radial access approach may improve access to areas that may otherwise be difficult to navigate using a right radial access or femoral access. Moreover, left radial access may improve trackability compared to right radial access. For example, a left radial approach to the heart may include one area of resistance near the left subclavian artery, whereas a right radial approach may include more areas of resistance, such as two areas of resistance near the right subclavian artery.

In some examples, the introducer extension may allow the clinician to position an effective access point (e.g., distal end of the introducer extension) to mimic that of a femoral access approach. Mimicking the femoral PCI approach may make it easier for a clinician trained in the femoral access approach to use a radial access approach, such as a left radial access approach. In this way, a left radial access approach with the described introducer extension may combine the benefits of a femoral access approach, such as improved device management compared to a radial access approach, ergonomic positioning of the clinician, and less radiation exposure to the clinician, with the benefits of a radial access approach, such as discussed above. For example, PCI devices (e.g., catheters and other PCI treatment devices) can be laid on patient and directed towards the patient's feet, which may reduce the number of devices hanging from or falling off an operating table. The clinician may have a reduced or no need to bend or reach over the patient. The clinician may be positioned near the legs or feet of the patient to increase distance from radiation emitting devices, such as a fluoroscope, positioned near the torso of the patient.

Additionally, in some examples, the introducer extension may couple to one or more supports that reduce movement of a portion of the patient's body, the introducer extension, or both during a PCI procedure. For example, in a radial access PCI procedure, the support may keep patient's arm from sagging or falling off the operating table, may position the patient's torso and/or reduce arm rotation such that the access site is facing the clinician. In some examples, the support includes an arm support that curves up and over the body of the patient to support the arm of the patient. The support may attach to the operating table. Alternatively, the support may be positioned under the patient or operating table mattress such that it is easily removed but held firmly by the body weight of the patient. The support also may optionally couple to the introducer extension to help maintain the position of the patient's arm and the introducer extender relative to the operating table and the patient's body. In this way, the support may eliminate need for a cushion or railing to support the arm of the patient. In some examples, the support may include an adjustable soft plastic attachment or adjustable strap to stabilize the arm of the patient.

FIG. 1 is a schematic and conceptual diagram illustrating an example medical assembly 100 including an introducer extension 114. In the example illustrated in FIG. 1, a patient 102 is positioned on an operating table 104. Patient 102 is in a supine position. In other examples, patient 102 may be in any other suitable position, such as a seated position or reclined position. Clinician 106 is positioned, e.g., standing, on the right side 103 of patient 102. Clinician 106 may be positioned on the right side of the patient 102 because of the floor plan or layout of an interventional catheterization laboratory room. For example, a fluoroscope or other medical device (not shown) may be positioned to the left of operating table 104 (from the patient's perspective). Space constraints or lack of hospital resources may make rearranging the interventional catheterization laboratory room for specific PCI procedures unreasonable.

As illustrated in FIG. 1, introducer extension 114 is configured to facilitate left radial access. Introducer extension 114 is coupled to a hub 112 of an introducer sheath 110. Introducer sheath 110 is inserted transdermally at left radial access site 108 into the left radial artery of patient 102. Introducer extension 114 includes a tubular sidewall extending from a proximal end to a distal end along a longitudinal axis and defining a lumen extending along the longitudinal axis. The distal end of introducer extension 114 is configured to mechanically couple to introducer sheath 110, e.g., via a coupling defined by hub 112. For example, introducer sheath 110, hub 112, and introducer extension 114 may define a common lumen. The common lumen is configured to allow passage of a medical device, such as a catheter or other PCI device along a length of introducer extension 114 and introducer sheath 110 into the radial artery.

In some examples, introducer extension 114 may be configured to define at least one curve 115 between the proximal end of the introducer extension and the distal end of the introducer extension. Curve 115 may be a fixed preformed curve or an adjustable curve. Curve 115 may enable clinician 106 to position the proximal end of introducer extension 114 (e.g., the effective access point) at a selected location, such as within region 116. In some examples, region 116 may be the same as or similar to a region of a femoral artery access site. In this way, introducer extension 114 may enable percutaneous access at a left radial access site 108 without clinician 106 bending over patient 102, which may not be ergonomic for clinician 106, and/or without positioning the left arm of the patient perpendicularly across the midline of patient 102, which may cause catheters or other PCI devices to extend beyond the edge of operating table 104.

In some examples, a padded support 120 may be positioned against a railing 118 of operating table 104 to prevent the arm of patient 102 from falling to the left side of patient 102, to improve the comfort of patient 102, or both. In other examples, a support may be used to restrain the arm of patient 102. The support may couple to introducer extension 114 to reduce movement of introducer extension 114 relative to the arm of patient 102.

Figure 2:
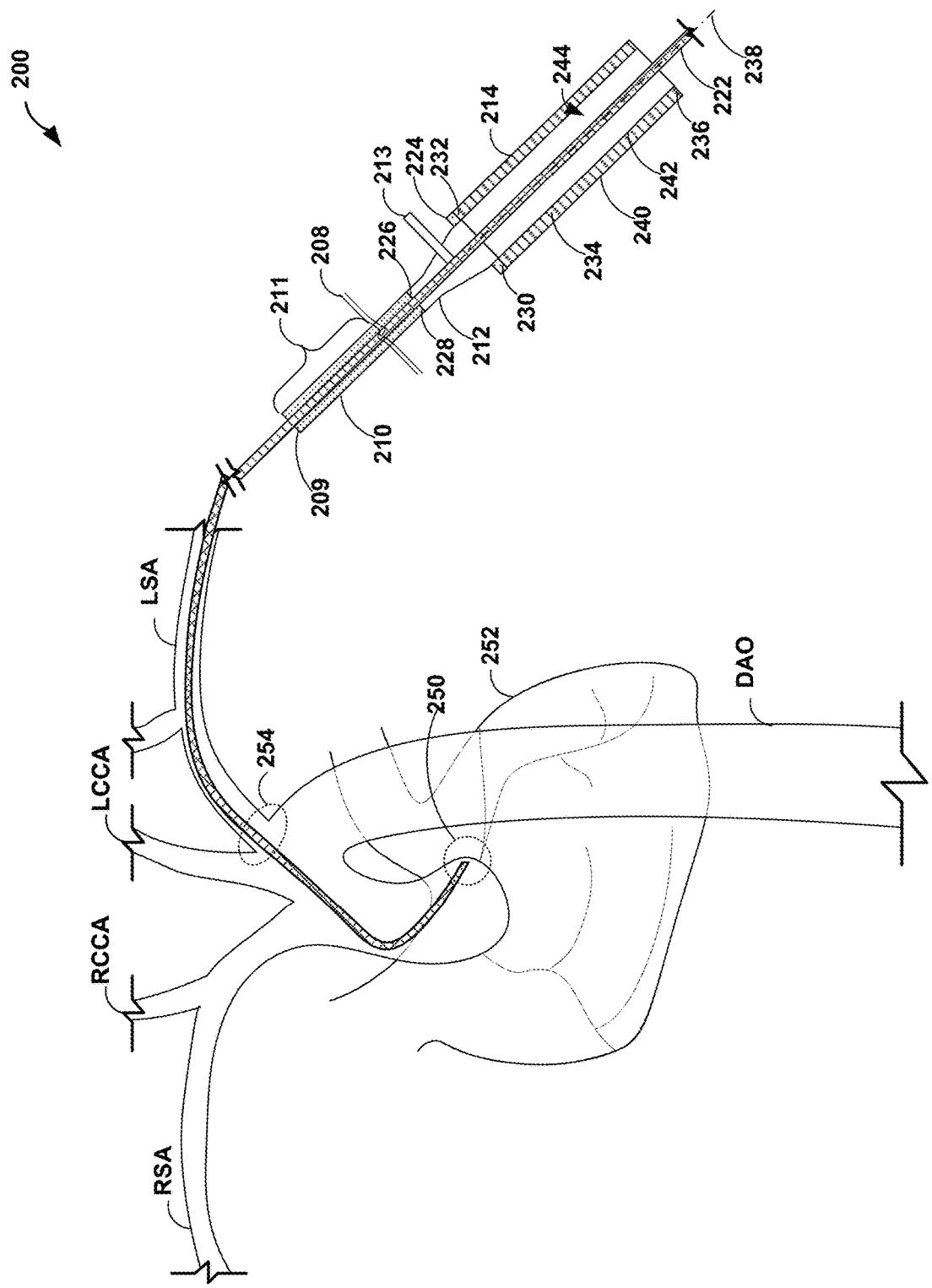
FIG. 2 is a conceptual diagram illustrating an example medical assembly including an introducer extension and a catheter.

FIG. 2 is a conceptual diagram illustrating an example medical assembly 200 including an introducer extension 214 and a catheter 222. Medical assembly 200 is configured for a PCI procedure, such as a left radial PCI procedure. Introducer extension 214 may be the same as or substantially similar to introducer extension 114 described above in reference to FIG. 1. For example, introducer extension 214 is coupled to hub 212 of introducer sheath 210. Introducer sheath 210 extends along longitudinal axis 238 from a distal end 209 to a proximal end 228. A distal portion 211 of introducer sheath 210 is configured to be inserted transdermally into vasculature of a patient, e.g., at access site 208.

In some examples, introducer sheath 210 may be integrally formed with hub 212. In other examples, introducer sheath 210 includes a discrete sheath, where a distal portion 226 of hub 212 is mechanically coupled to a proximal end 228 of the sheath. Hub 212 may include one or more ports 213. One or more ports 213 may include a valve, mechanical coupling, or both configured to pass fluid into a lumen of at least one of introducer sheath 210, hub 212, or introducer extension 214. Hub 212 includes a mechanical coupling 224. Distal end 232 of introducer extension 114 is configured to mechanically couple to introducer sheath 110, e.g., via mechanical coupling 224 defined by hub 112. For example, mechanical coupling may include any suitable coupling configured to fluidically couple a proximal end 230 of hub 212 to a distal end 232 of introducer extension 214.

Introducer extension 214 includes a tubular sidewall 234. Tubular sidewall 234 extends from a proximal end 236 of introducer extension 214 to distal end 232 along a longitudinal axis 238. Introducer extension 214 may include any suitable length. For example, a length of introducer extension 214 may be selected to extend from a wrist of a patient to a midsection of the patient. In some examples, a length of introducer extension 214 may be within a range from about 5 centimeters to about 50 centimeters, such as within a range from about 10 centimeters to about 40 centimeters. In some examples, a diameter of introducer extension 214 may be within a range from about 3 French (Fr) to about 8 Fr, such as within a range from about 4 Fr to about 7 Fr.

Tubular sidewall 234 includes an exterior surface 240 and an interior surface 242. Tubular sidewall 234 may include any suitable material. In some examples, tubular sidewall 234 may include a substantially rigid material or combination of materials. As used herein, substantially rigid means that the material will not bend or deform in response to a force having a magnitude equal to or less than the magnitude of forces typically applied to a PCI device, such as catheter 222. In other examples, tubular sidewall 234 may include a flexible material or combination of materials to facilitate positioning proximal end 236 at a desired location.

In some examples, tubular sidewall 234 may include a plurality of layers. For example, tubular sidewall 234 may include an inner layer and an outer layer. In some examples, tubular side wall 234 may include more than two layers, such as three layers or four layers, with one or more intermediate layers between the inner layer and the outer layer. In some examples, the inner layer may include a first lubricious polymer. The first lubricious polymer may include, for example, polytetrafluoroethylene (PTFE), high density polyethylene (HDPE), or the like. An inner layer including a first lubricious polymer may facilitate introduction of medical devices, such as catheter 222, through a lumen 244 of introducer extension 214. The outer layer may include a second polymer, such as polyamide, polyether block amide (PBA), or the like.

Interior surface 242 defines a lumen 244. Lumen 244 extends along longitudinal axis 238 of introducer extension 214. Lumen 244 is configured to allow passage of a medical device, such as catheter 222 or another PCI device. As discussed above, tubular side wall 234 may include a lubricious polymeric inner layer configured to allow a medical device to slide within lumen 244.

In some examples, tubular sidewall 234 may include a coil configured to provide structural stiffness, enable tubular sidewall 234 to retain a curved configuration, or both. The coil may include any number of filars, such as a single filar or two filars. The coil may include, for example, a medical grade metal, a shape memory alloy, stainless steel, a nickel titanium alloy, or another biocompatible metal or polymer. The coil may be embedded in tubular sidewall 234 or disposed on interior surface 242 or exterior surface 240. In examples in which tubular sidewall 234 includes a plurality of layers, the coil may be positioned on a radial outer surface of the inner layer and the outer layer may be positioned over the inner layer and the coil.

As illustrated in FIG. 2, introducer extension 214 may be used for a left radial access PCI procedure. In a left radial access PCI procedure, catheter 222 may be navigated through the left radial artery and left subclavian artery (LSA) to a target treatment site 250 within heart 252 of the patient. This pathway may include one area of resistance 254 near the ostium of the LSA. Having only one area of resistance may improve trackability of catheter 222 to target treatment site 250 compared to other PCI approaches (e.g., femoral or right radial PCI approaches). For example, a right radial artery approach via the right subclavian artery (RSA) may have at least two areas of resistance, a first area of resistance near the right common carotid artery (RCCA) and a second area of resistance near the ostium of the RSA. A femoral approach via the descending aorta (DAO) may have at least one area of resistance, a first area of resistance near that ostium of the LSA or left common carotid artery (LCCA), which may have a high degree of resistance because a catheter must follow to curve of the aorta. By reducing the areas of resistance, the degree of resistance, or both, left radial access may improve trackability of catheter 222 and, thereby, reduce operating time.

Figure 3A:
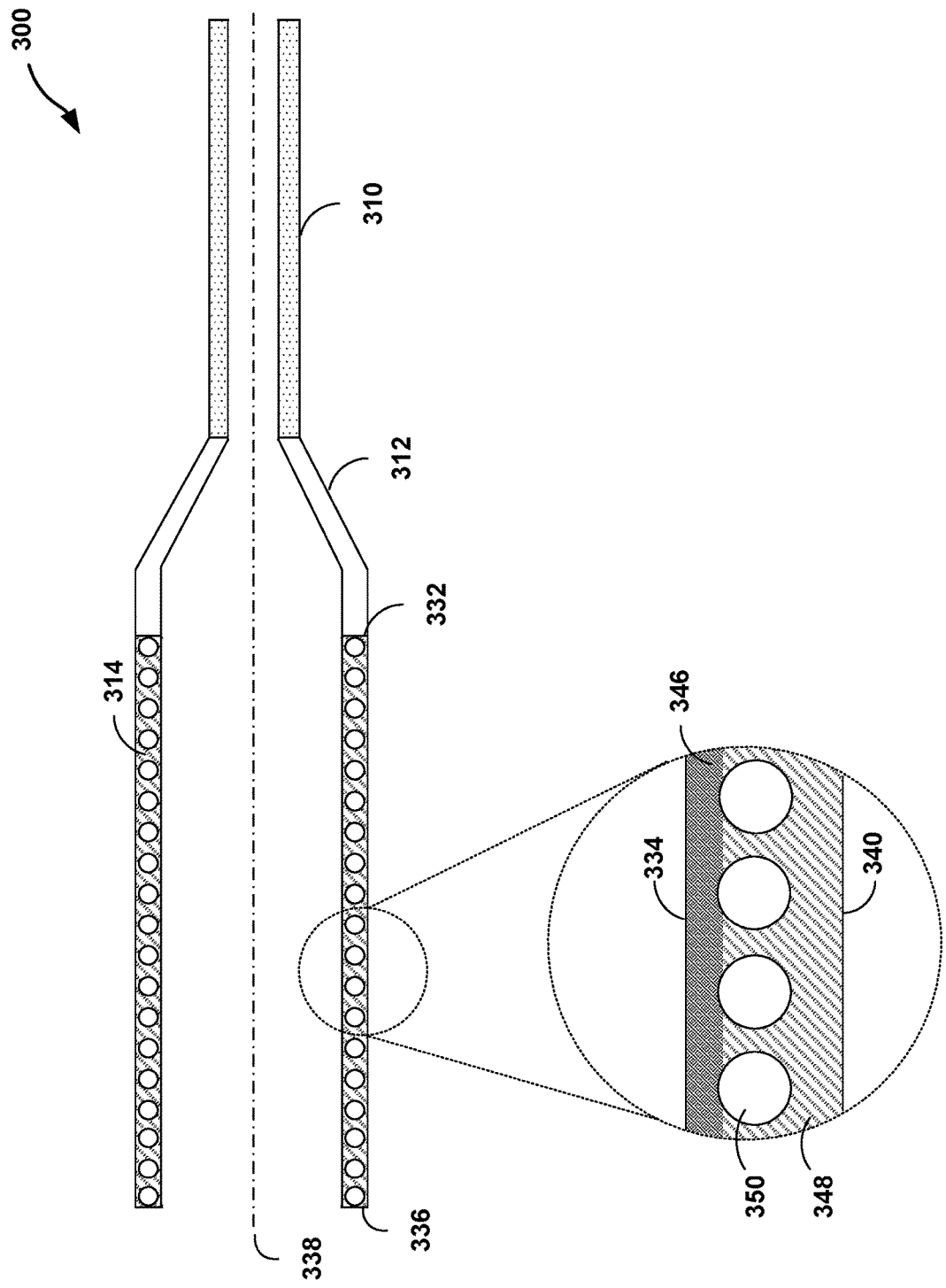
FIGS. 3A and 3B are conceptual diagrams illustrating an example medical assembly including an introducer sheath, a hub, and an introducer extension.
Figure 3B:
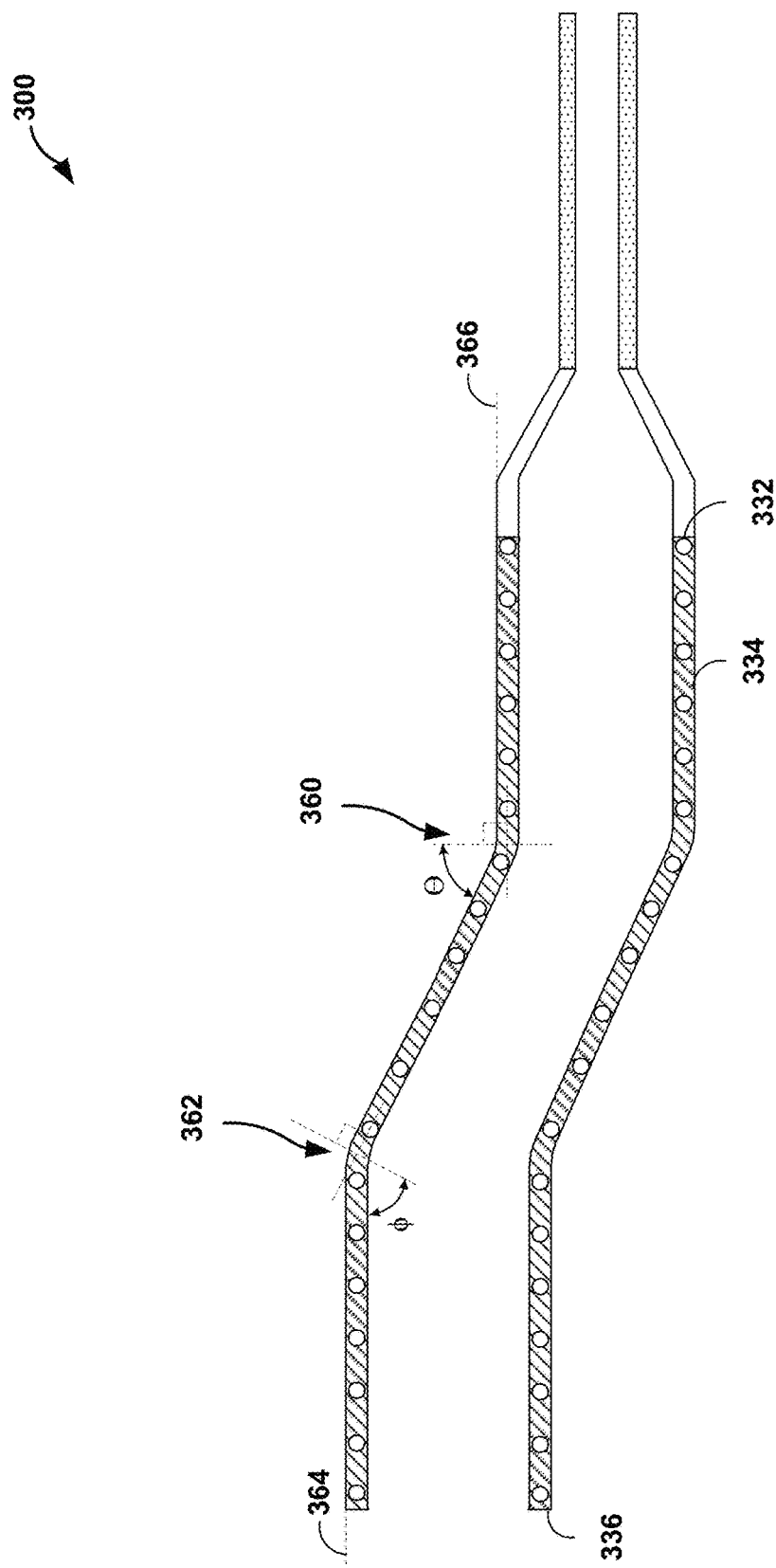

In some examples, an introducer extension, e.g., a tubular sidewall of an introducer extension, may be flexible, extendable, or both. FIGS. 3A and 3B are conceptual diagrams illustrating an example medical assembly 300 including an introducer sheath 310, a hub 312, and an introducer extension 314. Introducer extension 314 may be the same as or substantially similar to introducer extensions 114 and 214 described described above with reference to FIGS. 1 and 2, except for the differences described herein.

Introducer extension 314 is configured to have a variable length, a variable shape, or both. Introducer extension 314 includes a tubular sidewall 334. Tubular sidewall 334 includes an inner layer 346 and an outer layer 348. In some examples, tubular side wall 334 may include more than two layers. Inner layer 346 may include a lubricious polymer, an elastomeric polymer, silicon rubber, a thermoform polymer, polytetrafluoroethylene (PTFE), high density polyethylene (HDPE), or the like. Outer layer 348 includes a structural and/or protective polymer, such as, for example, an elastomeric polymer, silicon rubber, a thermoform polymer, polyamide, polyether block amide (PBA), or the like.

Tubular sidewall 334 also includes a single filar coil 350. Coil 350 may be configured to provide structural stiffness along a radial direction, longitudinal direction, or both; enable tubular sidewall 334 to retain a curved configuration; or both. Coil 350 may include any suitable material, such as, for example, a medical grade metal, a shape memory alloy, stainless steel, a nickel titanium alloy, or another biocompatible metal or polymer. Coil 350 may be formed on a radial outer surface of inner layer 346 and outer layer 348 may be formed over inner layer 346 and coil 350.

In some examples, tubular sidewall 334 is configured to expand and contract along longitudinal axis 338. For example, FIG. 3A illustrates introducer extension 314 in a contracted or collapsed configuration and FIG. 3B illustrates introducer extension 314 in an expanded configuration. Selected materials, structural configurations, or both may enable tubular sidewall 334 to expand and contract and retain the selected expanded or contracted configuration.

For example, as described above, tubular sidewall 334 may include one or more elastomeric polymers. The one or more elastomeric polymers may stretch and/or compress to enable the expanded and contracted configurations. In some examples, tubular sidewall 334 may include additional materials, such as coil 350, that enables tubular sidewall 334 to retain the expanded or contracted configuration. For example, when in the expanded configuration, coil 350 may resist the restorative force urging an elastomeric material of tubular sidewall 334 back to the contracted configuration.

In examples in which tubular sidewall 334 includes a structural configuration to enable the expanded and contracted configurations, the structural configuration may include an undulating surface. For example, tubular sidewall 334 may define an undulating surface having a plurality of alternating peaks and troughs. Each of the peaks and troughs may extend around a circumference of tubular sidewall 334 substantially transverse (e.g., transverse or nearly transverse within the limits of manufacturing techniques) to the longitudinal axis 338. The plurality of peaks and troughs may be configured to enable tubular sidewall 334 to fold and unfold at each of the peaks and troughs. For example, as peaks and troughs are unfolded, tubular sidewall 334 may expand. As peaks and troughs are folded, tubular side wall 334 may collapse.

In some examples, tubular sidewall 334 is configured to define at least one curve between proximal end 336 of introducer extension 314 and distal end 332 of introducer extension 314. In some examples, tubular sidewall 334 includes a preformed curved configuration. For example, tubular sidewall 334 may include a thermoform polymer that may be formed to have a fixed curved configuration. In other examples, tubular sidewall 334 may be configured to adjustably bend into a curved configuration (e.g., upon application of force by a clinician) and retain the curved configuration. As illustrated in FIG. 3B, the at least one curve may include a first curve 360 extending in a first direction and a second curve 362 extending in a second, different direction. Although illustrated as being in the plane of the page, first curve 360 and second curve 362 may be in different planes. By curving in different planes, the curve may enable introducer extension 314 to rest substantially flat against the contour of the body of a patient, allow a clinician to position the proximal end 336 of introducer extension 314 in a desired location, or both. The at least one curve may be defined by an angle having a selected arc degree. For example, first curve 360 may be defined by an angle θ and second curve 362 may be defined by angle φ. In some examples, the arc degree of first and second curves 360 and 362 may be within a range from about 0 degrees to about 90 degrees, such as about 0 degrees to about 60 degrees. It is understood that the arc degree may be expressed as an obtuse angle, for example, between about 90 degrees and about 180 degrees, such as between about 120 degree and about 180 degrees.

In some examples, introducer extension 314 may have a serpentine shape with multiple curves. In some examples, a first line 364 tangent to exterior surface 340 of introducer extension 314 at proximal end 336 and a second line 366 tangent to exterior surface 340 of introducer extension 314 at distal end 332 may be parallel or may meet at an angle within a range from about 0 degrees to about 90 degrees. In this way, introducer extension 314 is sufficiently bendable to provide an effective access site to the left radial artery that mimics the access site of a femoral access site.

FIGS. 4A-5B are conceptual diagrams illustrating example structural configurations of an introducer extension that allow an introducer extension to bend into a curved configuration and retain the curved configuration.

Figure 4A:
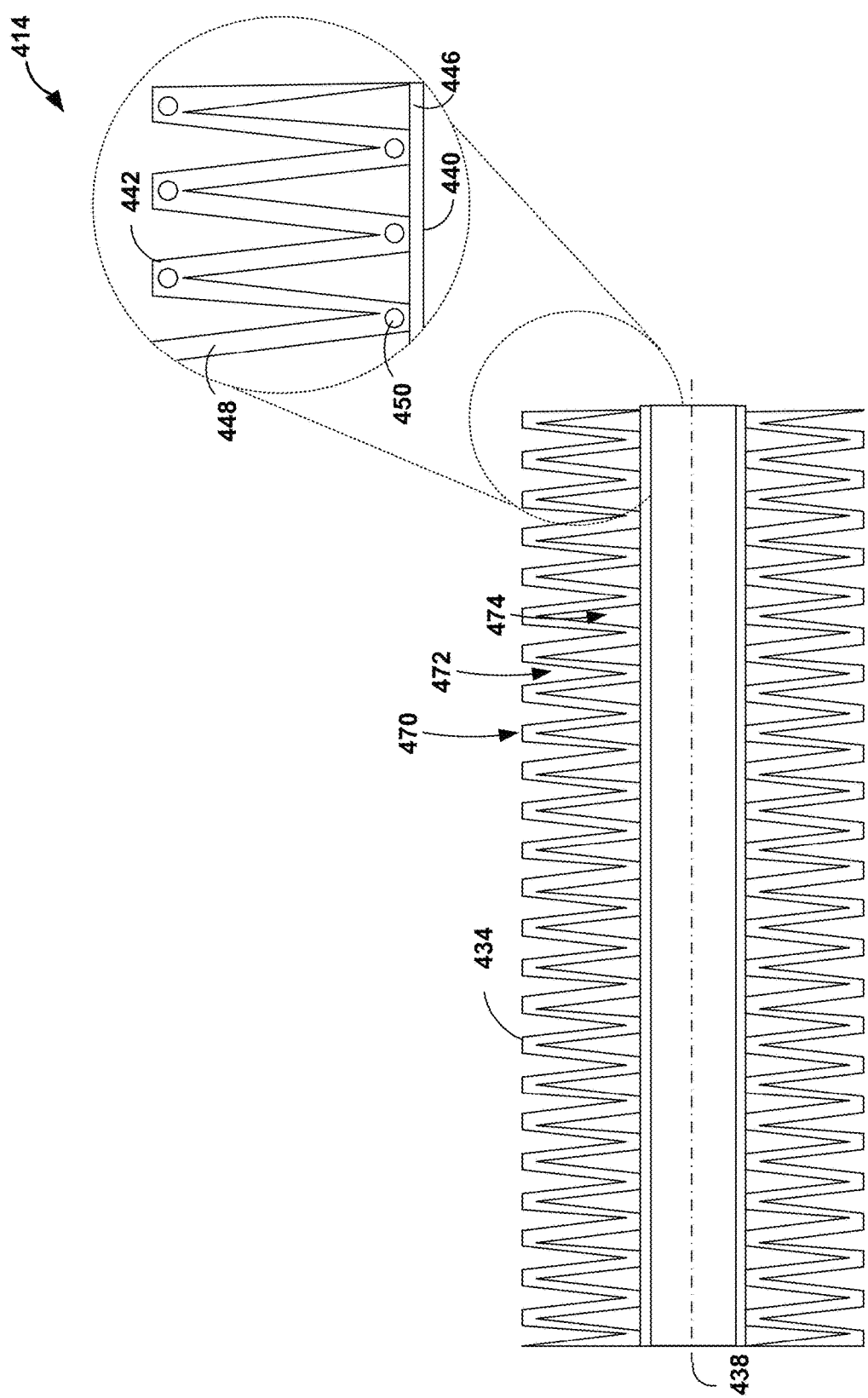
FIGS. 4A and 4B are conceptual diagrams illustrating an example structural configuration of an introducer extension that allows the introducer extension to bend into and retain a curved configuration.
Figure 4B:
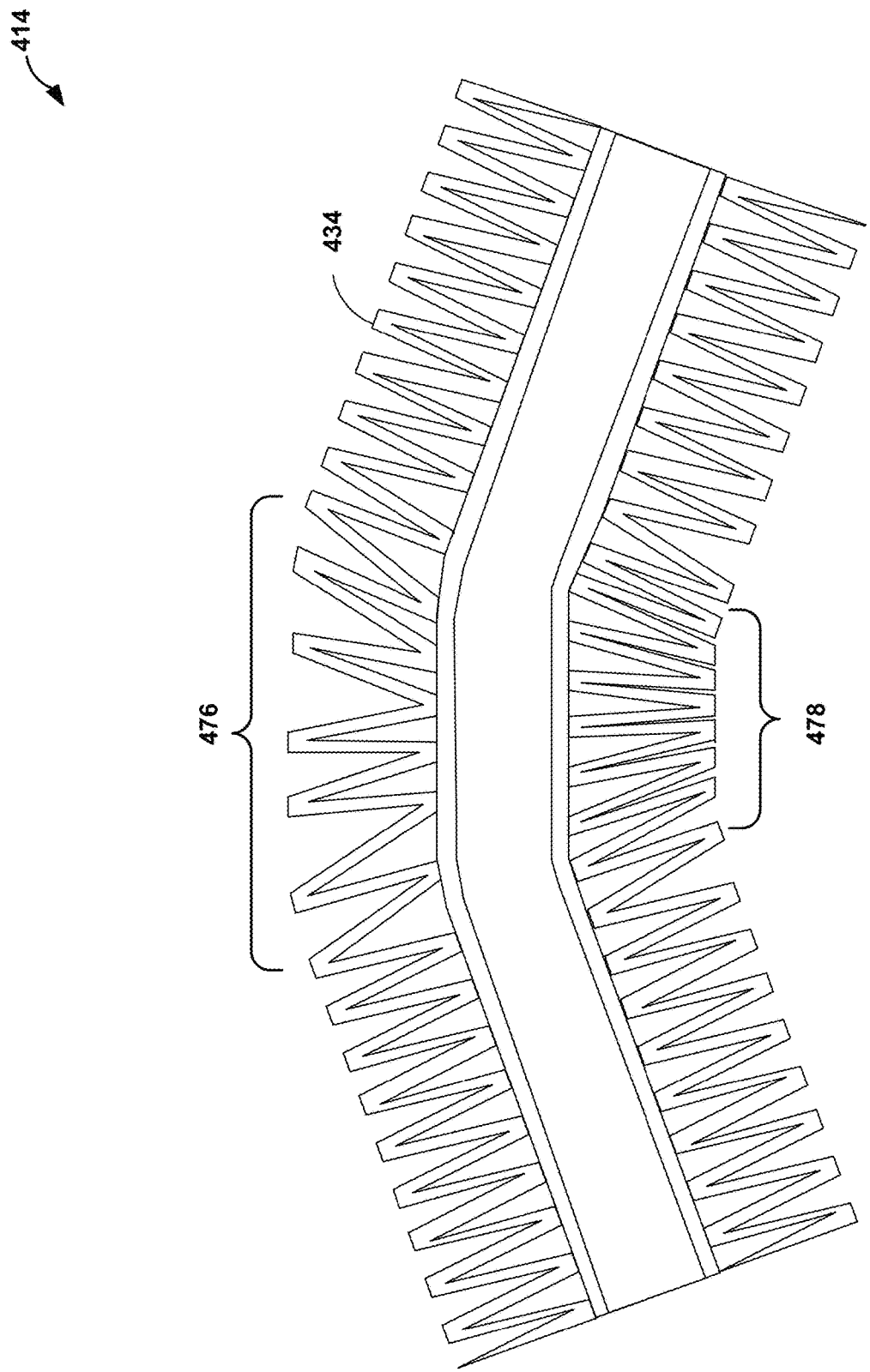

As illustrated in FIGS. 4A and 4B, introducer extension 414 includes tubular side wall 434. Introducer extension 414 may be the same as or substantially similar to introducer extensions 114, 214, and 314 described above in reference to FIGS. 1-3, except for the differences described herein. For example, tubular sidewall 434 may include an outer layer 448 defining an exterior surface 442 and an inner layer 446 defining an interior surface 440.

As illustrated in FIG. 4A, tubular sidewall 434 may include a structural configuration having an undulating surface (e.g., exterior surface 442) to enable tubular sidewall 434 to bend into a curved configuration. Undulating surface 442 defines a plurality of peaks 470 ("peaks 470") and a plurality of troughs 472 ("troughs 472"). Peak 470 and troughs 472 may extend around a circumference of tubular sidewall 434 transverse to the longitudinal axis 438. Areas 474 between adjacent peaks 470 and inner layer 446 may include any suitable material, such as, for example, fluid, air, water, or a substantially compressible material compared to enable relative movement between adjacent peaks 470 without significant resistance. Peaks 470 and troughs 472 are shaped to allow undulating surface 442 to fold into a collapsed configuration and unfold into an expanded configuration. For example, as illustrated in FIG. 4B, a curved configuration of introducer extension 414 may include an unfolded (expanded) region 476 and a folded (collapsed) region 478.

In some examples, tubular sidewall 434 also may include coil 450 or an additional material that resists a restorative force, thereby enabling tubular sidewall 434 to retain a curved configuration. Coil 450 may be configured to resist the restorative force urging tubular sidewall 334 back to a straight (un-curved) configuration. In some examples, undulating surface 442 may enable tubular sidewall 434 to retain a curved configuration without an additional material (e.g., coil 450) to resist a restorative force because the folded and unfolded portions of tubular sidewall 434 may sufficiently reduce any restorative force.

Figure 5A:
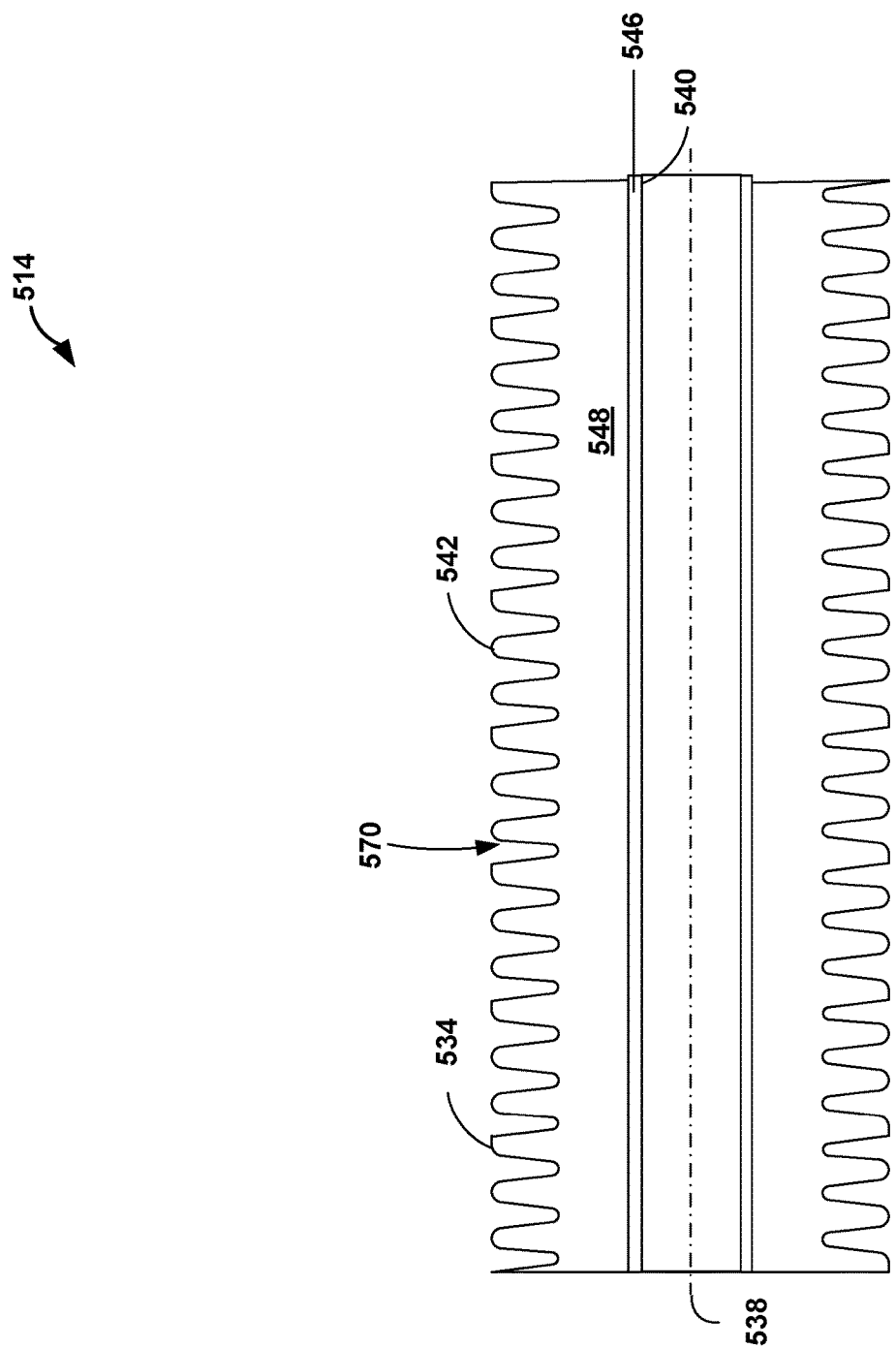
FIGS. 5A and 5B are conceptual diagrams illustrating an example structural configuration of an introducer extension that allows the introducer extension to bend into and retain a curved configuration.
Figure 5B:
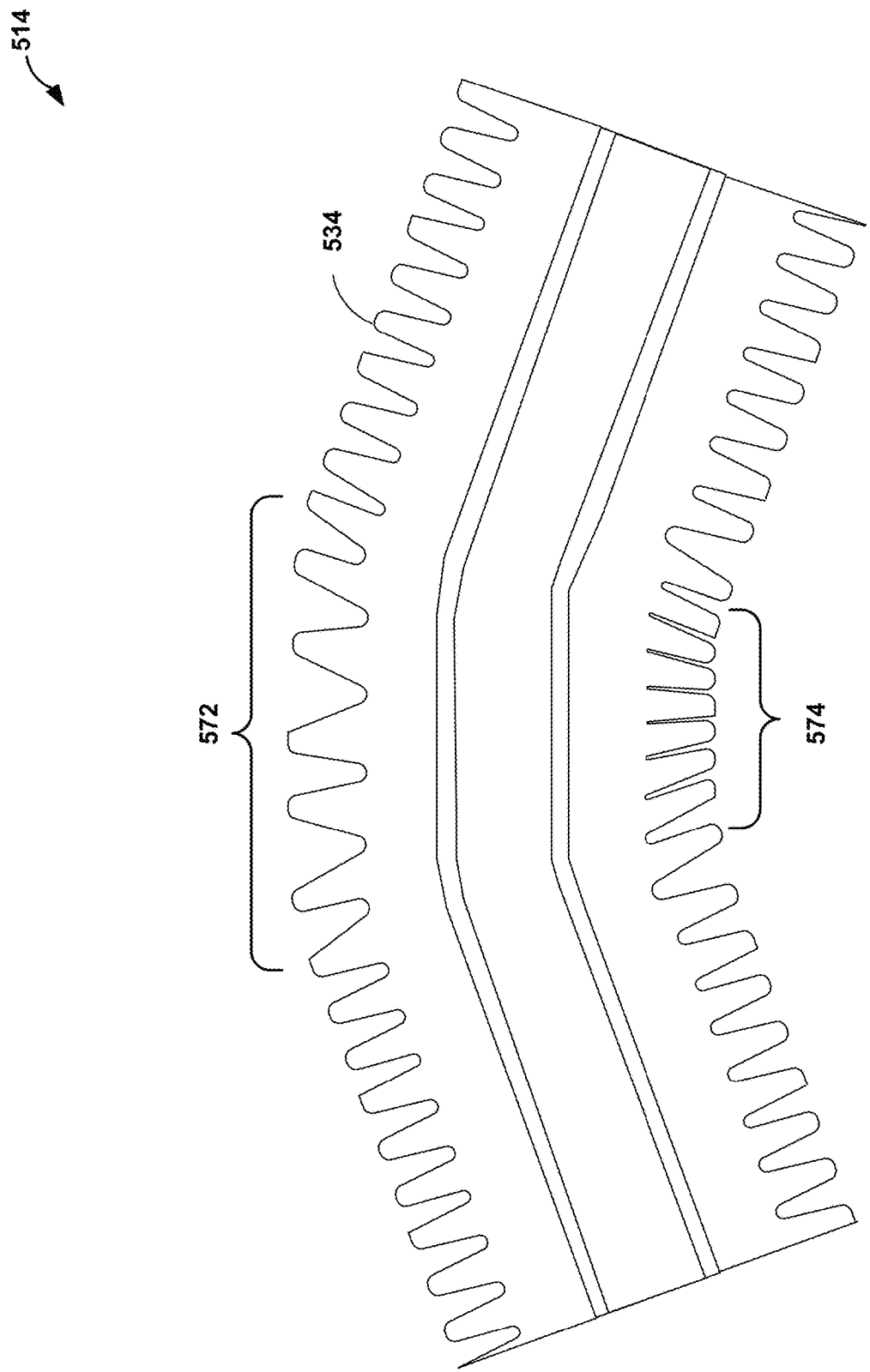

As illustrated in FIGS. 5A and 5B introducer extension 514 includes tubular side wall 534. Introducer extension 514 may be the same as or substantially similar to introducer extensions 114, 214, and 314 described above in reference to FIGS. 1-3, except for the differences described herein. For example, tubular sidewall 534 may include an outer layer 548 defining an exterior surface 542 and an inner layer 546 defining an interior surface 540.

As illustrated in FIG. 5A, tubular sidewall 534 may include a structural configuration having a plurality of grooves ("grooves 570") in exterior surface 542. Grooves 570 may be configured to enable tubular sidewall 534 to bend into a curved configuration. For example, as illustrated in FIG. 5B, the curved configuration may include an expanded region 572 and a compressed region 574. Grooves 570 may be shaped to reduce shear stress in response to bending of tubular sidewall 534 in at least one direction to enable tubular sidewall 534 to form expanded region 572 and a compressed region 574. In some examples, grooves 570 may extend around a circumference of tubular sidewall 534 transverse to the longitudinal axis 538. In some examples, grooves 570 may extend around less than an entire circumference of tubular sidewall 534 to in a direction that is not transverse to longitudinal axis 538 to control a direction in which tubular sidewall may bend. Grooves 570 may include any suitable shape, such as, for example, a rectilinear or curved shape. As discussed above with respect to expansion and contraction, tubular sidewall 534 with groove 570 may include an additional material that resists a restorative force, thereby enabling tubular sidewall 534 to retain a curved configuration.

Additionally, or alternatively, an introducer extension may include a moveable port configured to slide along the length of the introducer extension. FIGS. 6A-6E are conceptual diagrams illustrating a medical assembly 600 that includes an introducer extension 614 including a moveable port 680 configured to slide along the length of introducer extension 614. Introducer extension 614 may be the same as or substantially similar to introducer extensions 114, 214, 314, 414, and 514 discussed above in reference to FIGS. 1-5B, except for the differences described herein. For example, introducer extension 614 may be coupled to introducer sheath 610 and hub 612.

As illustrated in FIG. 6A, tubular sidewall 634 extends from proximal end 636 to distal end 632 and defines a slit 684 extending along longitudinal axis 638. Moveable port 680 defines an outer surface 682 and an inner surface 690 (FIG. 6E) extending from a proximal face 688 to a distal face 686. Outer surface 682 may be configured to be manipulated by a clinician. For example, outer surface 682 may be shaped to allow a clinician to grasp outer surface 682. Inner surface 690 is configured to at least partially surround tubular sidewall 634 in sliding engagement in the longitudinal direction. For example, inner surface 690 may extend around at least 50% of a circumference of tubular sidewall 634. In some examples, as illustrated in FIG. 6B, movable port 680 may be configured to travel over curves 660 and 662 in tubular sidewall 634. For example, an inner diameter of moveable port 680 may be larger than an outer diameter of tubular sidewall 634 to enable moveable port to travel over curves 660 and 662. In some examples, an inner diameter of moveable port 680 may be between about 1% to about 20% larger than an outer diameter of tubular sidewall 634.

Figure 6D:
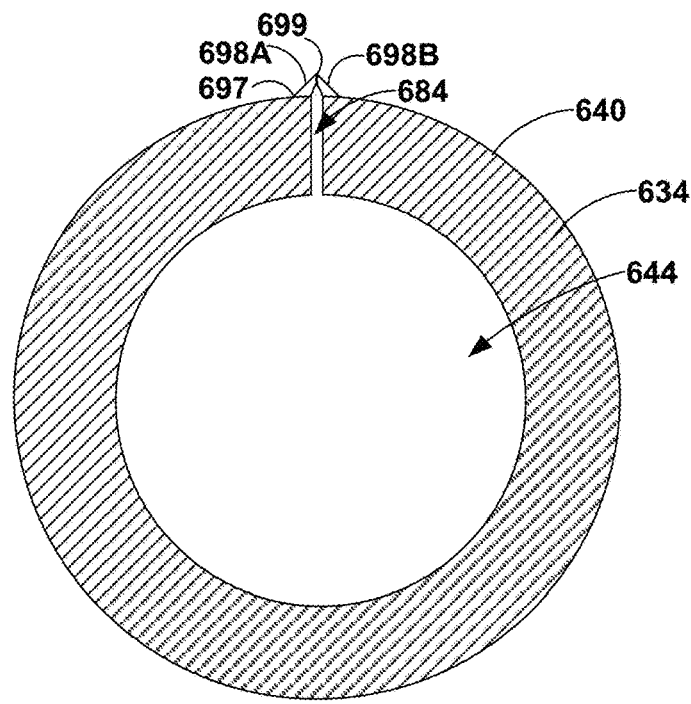

As illustrated in FIG. 6C, moveable port 680 includes a tubular member 692. Tubular member 692 extends from a proximal end 693 at a first aperture 694 on outer surface 682 to a distal end 695 at a second aperture 696. Distal end 695 may be positioned at or near a plane defined by distal face 686 or may be positioned distal or proximal to the plane defined by distal face 686. Distal end 695 of tubular member 692 may be substantially parallel to longitudinal axis 638. Proximal end 693 of tubular member 692 may be substantially perpendicular to longitudinal axis 638. Tubular member 692 is sized to allow passage of a medical device, such as, for example, a catheter. Tubular member 692 extends through slit (FIG. 6D) such that a lumen 693 of tubular member 692 is fluidically coupled to lumen 644 of tubular sidewall 634.

Moveable port 680 is moveable along slit 684 to adjust a longitudinal position of tubular member 692. Tubular sidewall 634 may include a resilient material configured to deform around a circumference of the tubular member 692 of moveable port 680. For example, slit 684 may remain closed or nearly closed distal and proximal to movable port 680 as moveable port is moved along longitudinal axis 638. In this way, a clinician may control a distance from introducer sheath 610 to tubular member 692.

Figure 6E:
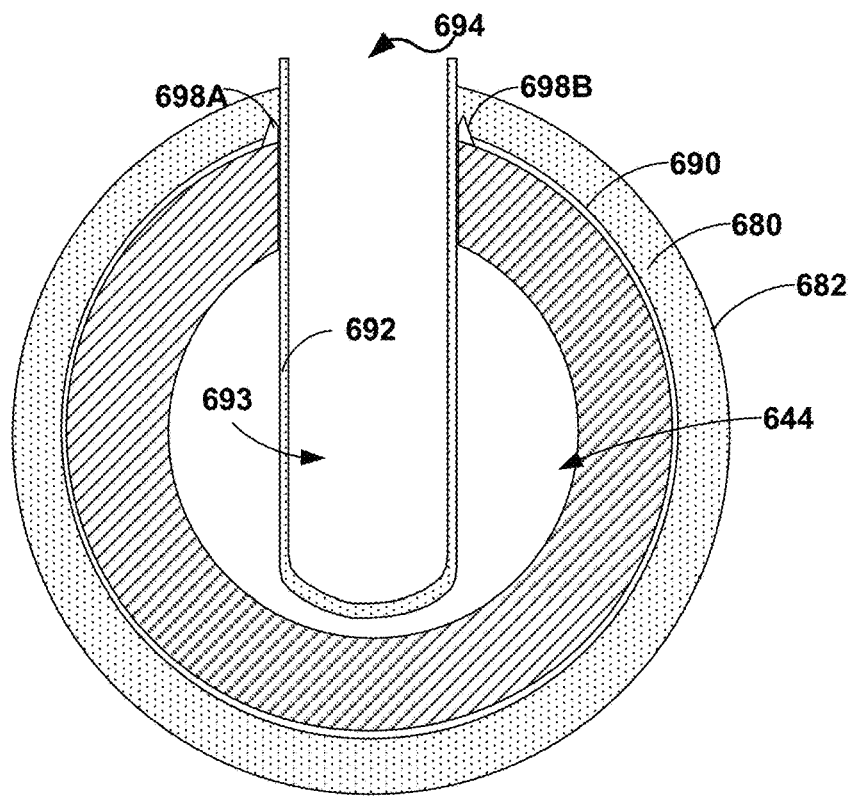

In some examples, as shown in FIGS. 6D and 6E, tubular sidewall 634 may include one or more flaps 698A, 698B extending along longitudinal axis 638 (FIGS. 6A and 6C) on outer surface 640 of tubular sidewall 634 and extending circumferentially around a portion of outer surface 640 from a first edge fixed to outer surface 640, over slit 684, to a second free edge. For example, tubular sidewall 634 may include a pair of flaps 698A and 698B, each extending along longitudinal axis 638 on outer surface 640 of tubular sidewall 634 and extending circumferentially around a portion of outer surface 640 from a first edge fixed 697 to a second free edge 699 at slit 684.

Figure 6F:
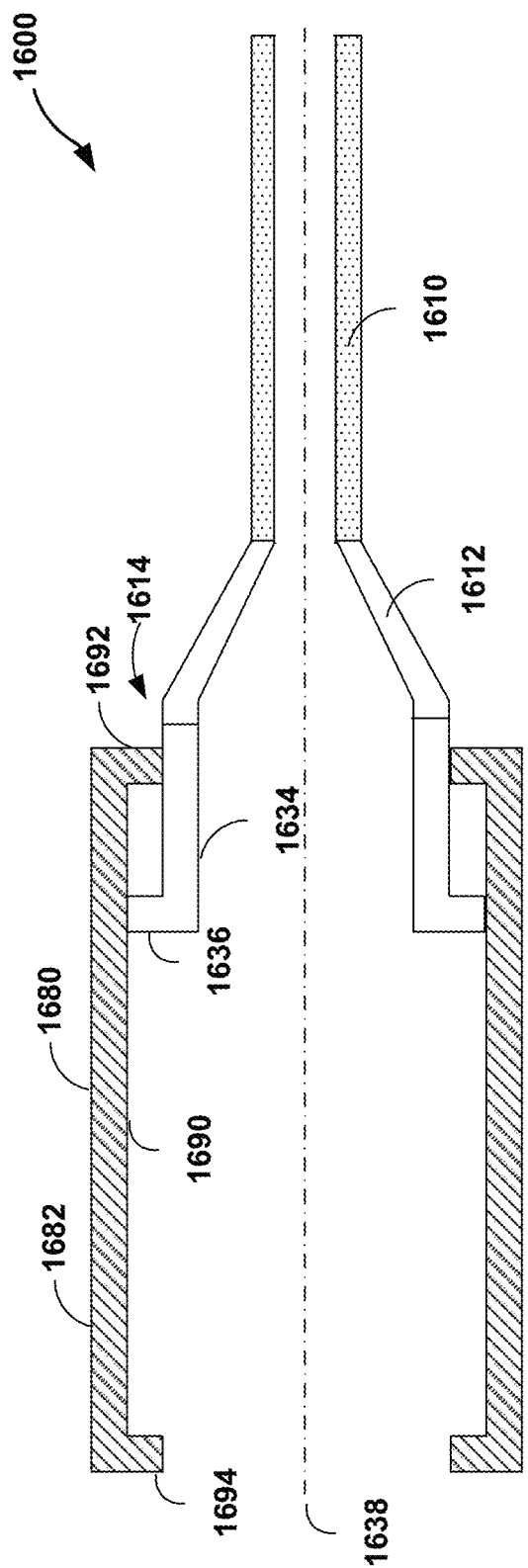

In some examples, the moveable port and the tubular sidewall may define an adjustable syringe-like assembly. FIG. 6F is a conceptual diagram illustrating a medical assembly 1600 that includes an introducer extension 1614 including a moveable port 1680 configured to slide relative to tubular sidewall 1634 along longitudinal axis 1638. Introducer extension 614 may be the same as or substantially similar to introducer extensions 114, 214, 314, 414, 514, and 614 discussed above in reference to FIGS. 1-6E, except for the differences described herein. For example, introducer extension 614 may be coupled to introducer sheath 1610 and hub 1612.

For example, as illustrated in FIG. 6F, tubular sidewall 1634 is slidably engaged with inner surface 1690 of moveable port 1680. Outer surface 1682 may be configured to be manipulated by a clinician. For example, outer surface 1682 may be shaped to allow a clinician to grasp outer surface 1682 to slide moveable port 1680 relative to tubular sidewall 1634. Inner surface 1690 may define a first lip 1692 and a second lip 1694 configured engage a corresponding lip 1636 on tubular sidewall. For example, when in a distal-most position of moveable port 1680, relative to tubular sidewall 1634, first lip 1692 may engage lip 1636. When in a proximal-most position of moveable port 1680, relative to tubular sidewall 1634, second lip 1694 may engage lip 1636. As discussed above, at least one of moveable port 1680 and/or tubular sidewall 1634 may be formed using axial metal wire (e.g., copper wire) embedded with in a molded (e.g., injection molded) polymeric sidewall. The axial metal wire may improve shape retention.

Figure 7:
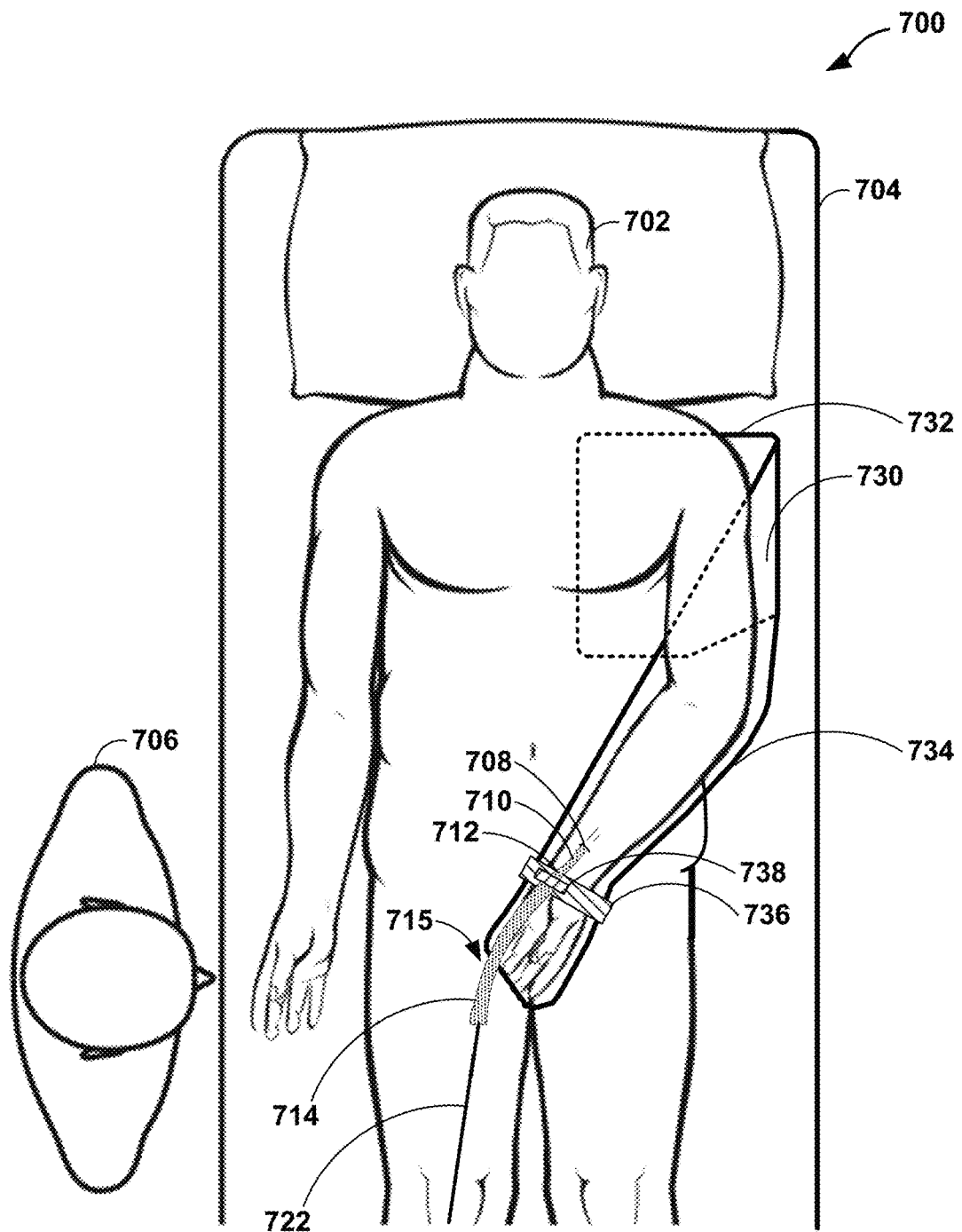
FIG. 7 is a conceptual diagram illustrating an example medical assembly including an introducer extension and a support.

In some examples, a medical assembly may include a support configured to couple to an introducer extension. FIG. 7 is a conceptual diagram illustrating an example medical assembly 700 including an introducer extension 714 and a support 730. Medical assembly 700 may be the same as or substantially similar to medical assembly 100 described above in references to FIG. 1, except for the differences described herein. Introducer extension 714 may be the same as or substantially similar to any of introducer extensions 114, 214, 314, 414, 514, or 614 described above in references to FIGS. 1-6E. For instance, introducer extension 714 is coupled to a sheath 710 at a left radial access site 708 for introduction of a catheter 722. Introducer extension 714 includes a curved configuration 715.

In the example illustrated in FIG. 7, a patient 702 is positioned on an operating table 704. Patient 702 is in a supine position. In other examples, patient 702 may be in any other suitable position, such as a seated position or reclined position. Clinician 706 is positioned, e.g., standing, on the right side of patient 702.

Support 730 is configured to restrain a portion of the body of patient 702, such as the left arm of patient 702. For example, support 730 may include a rigid plastic arm stabilizer. In some examples, support 730 may include other materials, such as a metal, or additional materials, such as flexible polymeric portions or metal reinforcing portions. Support 730 includes a first portion 732 configured to be placed under a portion of patient 702. For example, when patient 702 is in a supine position, first portion 732 may be positioned under the torso of patient 702 or under a mattress of operating table 704. Support 730 includes a second portion 734 extending from first portion 732 and configured to engage an arm of patient 702. Second portion 734 may reduce at least one of external abduction or external rotation of the arm of patient 702. In some examples, second portion 734 may be configured to position a wrist of patient 702 near a midsection of patient 702.

In some examples, support 730, e.g., second portion 734 may include a retention device 736. Retention device 736 may be configured to, when engaged, limit the mobility of the arm of patient 702. For example, retention device 736 may include a strap and a fastener. The fastener may include, for example, at least one of a hook and loop fastener, a button, or a buckle.

In some examples, introducer extension 714 or hub 712 may include at least one attachment member 738 configured to engage support 730 or retention device 736. For example, attachment member 738 may include a strap and a fastener, such as, for example, at least one of a hook and loop fastener, a button, or a buckle. In some examples, attachment member 738 may include a mechanical coupling configured to releasable couple to retention device 736.

Figure 8:
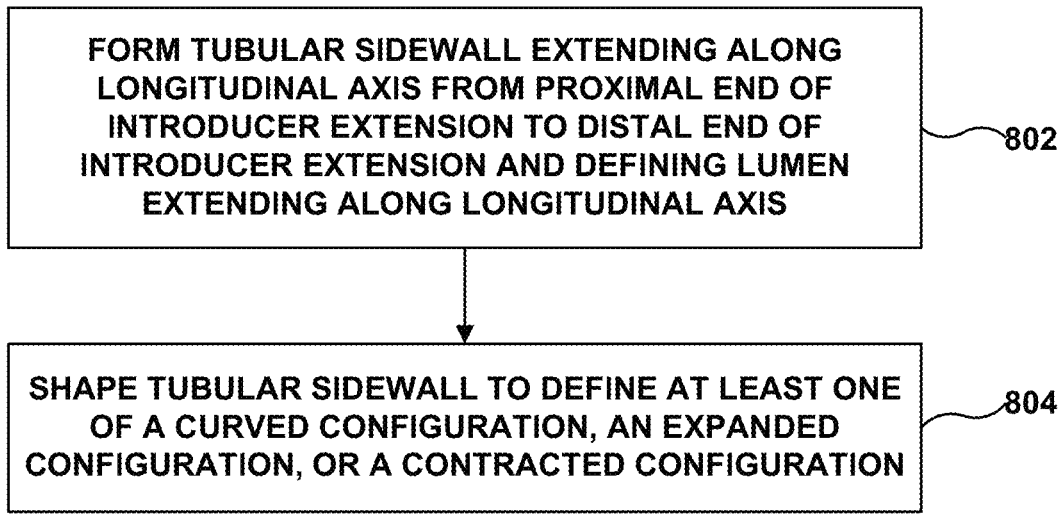
FIG. 8 is a flow diagram illustrating an example method of manufacturing an introducer extension of medical assembly.

The medical assemblies and introducer extensions described herein may be manufactured using any suitable technique. FIG. 8 is a flow diagram illustrating an example method of manufacturing an introducer extension of medical assembly. Although the technique illustrated in FIG. 8 is described in reference to the medical assemblies and introducer extensions described in reference to FIGS. 1-7, the technique may be used to manufacture other medical assemblies and introducer extensions. Additionally, medical assemblies and introducer extensions described in reference to FIGS. 1-7 may be manufactured using other techniques.

The technique illustrated in FIG. 8 includes forming tubular sidewall 234 extending along longitudinal axis 238 from proximal end 236 of introducer extension 214 to distal end 232 of introducer extension 214 and defining lumen 244 extending along longitudinal axis 238 (802). Tubular sidewall 234 is configured to define curved configuration 115 having at least one curve between proximal end 236 and distal end 232. Distal end 232 is configured to couple to introducer sheath 210 or hub 212. Lumen 244 is configured to allow passage of a medical device, such as catheter 222.

In example in which tubular sidewall 334 includes a plurality of layers, the technique may include forming inner layer 346 and forming outer layer 348 on a radial outer surface of inner layer 346. In some examples, as described above, inner layer 346 may include a first lubricious polymer and outer layer 348 may include a second, different polymer. In example in which tubular sidewall 334 includes coil 350, forming tubular sidewall 334 may include forming coil 350 on a radial outer surface of inner layer 346, and forming outer layer 348 over inner layer 346 and coil 350.

In some examples, forming tubular sidewall 234 may include forming exterior surface 242 of tubular sidewall 234 to adjustably bend into the curved configuration 115. In some examples, forming tubular sidewall 34 may include forming a surface 240 and/or 242 of tubular sidewall 234 to expand and contract along longitudinal axis 238. In some examples, forming tubular sidewall 434 may include forming tubular sidewall 434 to define a plurality of peaks 470 and a plurality of troughs 472, each of peaks 470 and troughs 472 extending around a circumference of tubular sidewall 434 transverse to longitudinal axis 438. As described above, peaks 470 and troughs 472 may be configured to fold and unfold. In some examples, forming tubular sidewall 534 may include forming a plurality of grooves 570 in exterior surface 542 of tubular sidewall 534. As described above, grooves 570 may be configured to reduce shear stress in response to bending of tubular sidewall 534 in at least one direction.

The technique illustrated in FIG. 8 also includes shaping tubular sidewall 234 to define at least one of curved configuration 115, an expanded configuration, or a contracted configuration (804). For example, a bending force may be applied to tubular sidewall 234. In examples in which the tubular sidewall includes a substantially rigid plastic, shaping the tubular sidewall may include thermoforming the tubular sidewall to define a substantially rigid preformed curve. Thermoforming may include applying a bending force to tubular sidewall 234 and applying heat to tubular sidewall 234. In some examples, as discussed above, tubular sidewall 234 may be expanded into an expanded configuration or collapsed into a contracted (collapsed) configuration.

Figure 9:
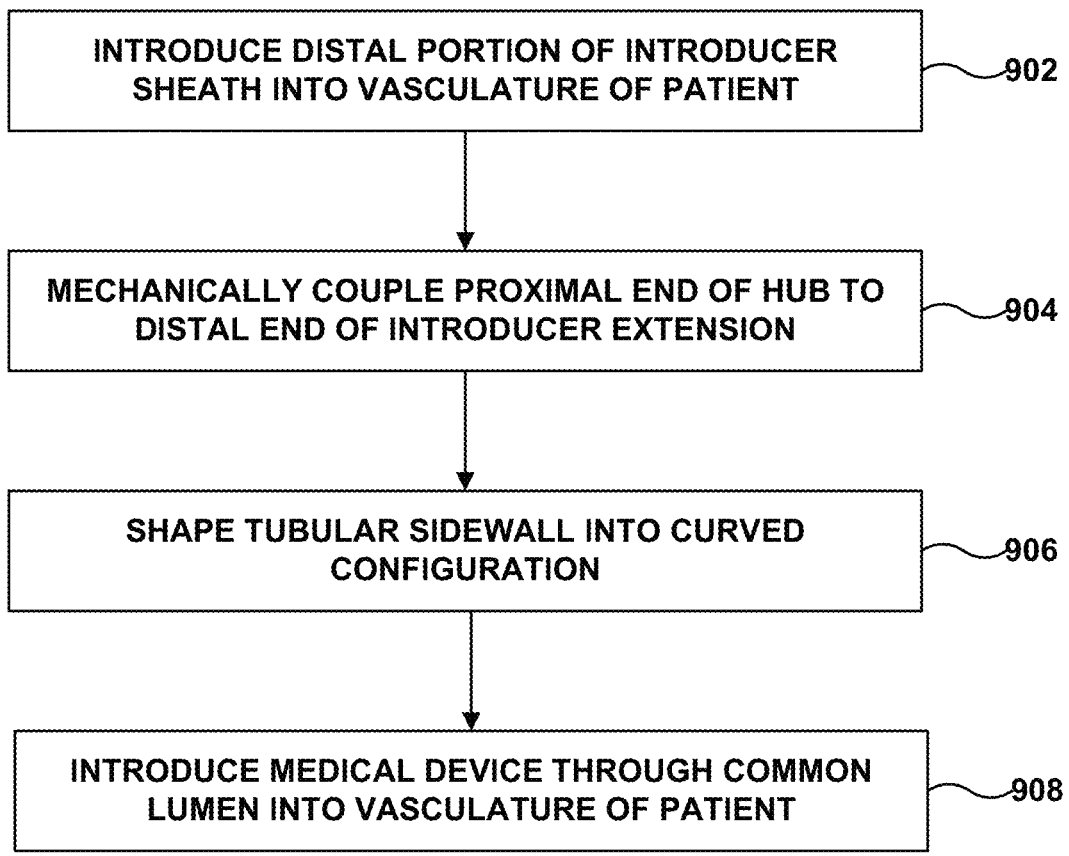
FIG. 9 is a flow diagram illustrating an example method of using the described medical assemblies including an introducer extension to perform percutaneous coronary intervention (PCI) procedures.

The medical assemblies and introducer extensions described herein may be used to perform PCI procedures using any suitable technique. FIG. 9 is a flow diagram illustrating an example method of using the described medical assemblies including an introducer extension to performed PCI procedures. Although the technique illustrated in FIG. 9 is described in reference to the medical assemblies and introducer extensions described in reference to FIGS. 1-7, the technique may be used to manufacture other medical assemblies and introducer extensions. Additionally, medical assemblies and introducer extensions described in reference to FIGS. 1-7 may be used other in other medical procedures that include transdermal insertion of a medical device into the body of a patient.

The technique illustrated in FIG. 9 includes introducing distal portion 211 of introducer sheath 210 into vasculature of patient 102 (902). As discussed above, introducer sheath 210 extends along longitudinal axis 238 from distal end 209 of introducer sheath 210 to proximal end 228 of introducer sheath 210. Proximal end 228 of introducer sheath 210 may be coupled to distal end 226 of hub 212 extending from distal end 226 of hub 212 to proximal end 230 of hub 212. In some examples, introducer sheath 210 may be introduced into the vasculature via an incision in an artery of patient 102, such as the left radial artery of patient 102. In some examples, introducer sheath 210 may include an incisive tip configured to penetrate the dermis and arterial wall.

The technique illustrated in FIG. 9 includes mechanically coupling proximal end 230 of hub 212 to distal end 232 of introducer extension 214 (904). As discussed above introducer extension 214 may include tubular sidewall 234 extending along longitudinal axis 238 from proximal end 232 of introducer extension 214 to distal end 236 of introducer extension 214. Tubular sidewall 234 may be configured to define a curved configuration (e.g., curved configuration 115) having at least one curve between proximal end 232 of introducer extension 214 and distal end 236 of introducer extension 214. Introducer sheath 210, hub 212, and introducer extension 214 may define common lumen (e.g., lumen 244).

The technique illustrated in FIG. 9 includes shaping tubular sidewall 234 into curved configuration 115 (906). In some examples, shaping tubular sidewall 234 into curved configuration 115 may include shaping tubular sidewall 234 into a first curve (e.g., curve 360) extending in a first direction and a second curve (e.g., curve 362) extending in a second, different direction. In some examples, curved configuration 115 may include any number of curves in one or more directions. By shaping tubular sidewall 234, a clinician may adjust a shape of introducer extension 214 to conform to a shape of the body of patient 102, to better match the clinician's preference, or both. In examples in which tubular sidewall 234 is configured to expand and contract along longitudinal axis 234, shaping tubular sidewall 234 into curved configuration 115 may include expanding tubular sidewall 234 along longitudinal axis 238.

The technique illustrated in FIG. 9 includes introducing a medical device (e.g., catheter 222) through the common lumen 244 into the vasculature of patient 102 (908). For example, catheter 222 may be introduced into the left radial artery of patient 102 and advanced to a target treatment site 250 at a heart 252 of patient 102.

In examples in which tubular sidewall 634 defines slit 684 extending along longitudinal axis 638 and introducer extension 614 includes moveable port 680, as described above, the technique may include moving moveable port 680 along tubular sidewall 634, e.g., in the direction of longitudinal axis 638, to a target position. The target position may include a position selected by a clinician. For example, the target position may include a region that mimics the region a femoral access site, e.g., region 116.

As discussed above in reference to FIG. 7, medical assembly 700 may include support 730. Support 730 includes first portion 732 configured to be placed under a patient and second portion 734 extending from first portion 730 and configured to engage an arm of patient 102. A body weight of patient 102 against first portion 730 may stabilize second portion 732 to reduce or prevent at least one of movement of the arm of patient 102, external abduction of the arm of patient 102, or external rotation of the arm of patient 102. In some examples, second portion 734 may include retention device 736 configured to, when engaged, limit the mobility of the arm of patient 702. In examples in which the medical assembly includes support 730, the technique illustrated in FIG. 9 may include securing an arm of patient 102 to support 730 using retention device 736. In examples in which hub 712 includes at least one attachment member 738 configured to engage support 730, the technique also may include securing at least one attachment member 738 to support 730.

The following clauses include example subject matter based on the disclosure.

Clause 1. An introducer extension comprising: a tubular sidewall extending along a longitudinal axis from a proximal end of the introducer extension to a distal end of the introducer extension and defining a lumen extending along the longitudinal axis, wherein the tubular sidewall is configured to define a curved configuration having at least one curve between the proximal end and the distal end, wherein the distal end is configured to couple to an introducer sheath, and wherein the lumen is configured to allow passage of a medical device.

Clause 2. The introducer extension of clause 1, wherein the at least one curve comprises a first curve extending in a first direction and a second curve extending in a second, different direction.

Clause 3. The introducer extension of clause 1 or 2, wherein the at least one curve is defined by an arc degree within a range from about 0 degrees to about 90 degrees.

Clause 4. The introducer extension of any one of clauses 1 through 3, wherein the tubular sidewall is configured to adjustably bend into the curved configuration, wherein the tubular sidewall is configured to retain the curved configuration.

Clause 5. The introducer extension of any one of clauses 1 through 4, wherein the tubular sidewall is configured to expand and contract along the longitudinal axis.

Clause 6. The introducer extension of any one of clauses 1 through 5, wherein the tubular sidewall comprises a substantially rigid plastic.

Clause 7. The introducer extension of any one of clauses 1 through 6, wherein the tubular sidewall defines a plurality of peaks and troughs, each of the peaks and troughs extending around a circumference of the tubular sidewall substantially transverse to the longitudinal axis.

Clause 8. The introducer extension of clause 7, wherein the plurality of peaks and troughs are configured to fold and unfold to at least one of expand and contract the tubular sidewall along the longitudinal axis or adjustably bend into the curved configuration.

Clause 9. The introducer extension of any one of clauses 1 through 8, wherein an exterior surface of the tubular sidewall defines a plurality of grooves, wherein the plurality of grooves is configured to reduce shear stress in response to bending of the tubular sidewall in at least one direction.

Clause 10. The introducer extension of any one of clauses 1 through 9, wherein the tubular sidewall comprises a plurality of layers.

Clause 11. The introducer extension of any one of clauses 1 through 10, wherein the plurality of layers comprises: an inner layer comprising a first, lubricious polymer; and an outer layer comprising a second, different polymer.

Clause 12. The introducer extension of clause 11, wherein the inner layer comprises at least one of polytetrafluoroethylene, or high-density polyethylene, and wherein the outer layer comprises at least one of a polyamide or a polyether block amide.

Clause 13. The introducer extension of any one of clauses 10 through 12, wherein the tubular sidewall comprises a coil formed on a radial outer surface of a first layer of the plurality of layers, and wherein a second layer of the plurality of layers is formed over the first layer and the coil.

Clause 14. The introducer extension of clause 13, wherein the coil comprises at least one of stainless steel or nickel titanium alloy.

Clause 15. The introducer extension of any one of clauses 1 through 14, wherein a length of the introducer extension is configured to extend from a wrist of a patient to a midsection of the patient.

Clause 16. The introducer extension of clause 15, wherein the introducer extension is configured to extend from a left wrist of a patient to a midsection of the patient with a proximal end of the lumen oriented toward a left side of the patient.

Clause 17. The introducer extension of any one of clauses 1 through 16, wherein the tubular sidewall defines a slit extending along the longitudinal axis, and wherein the of the introducer extension further comprises a moveable port comprising: an annular body having an outer surface and an inner surface, each extending from a proximal face to a distal face, wherein the outer surface is configured to be manipulated by a clinician, and wherein the inner surface is configured to at least partially surround the tubular sidewall in sliding engagement; and a tubular member extending from a proximal end at a first aperture defined by the outer surface to a distal end, wherein the tubular member extends through the slit such that a lumen of the tubular member is fluidly coupled to the lumen of the tubular sidewall, wherein the moveable port is moveable along the tubular sidewall to adjust a longitudinal position of the tubular member.

Clause 18. The introducer extension of clause 17, wherein the lumen of the tubular member at the distal end is substantially parallel to the longitudinal axis, wherein the lumen of the tubular member at the proximal end is substantially perpendicular to the longitudinal axis.

Clause 19. The introducer extension of clause 17 or 18, wherein the tubular sidewall comprises a resilient material configured to deform around a circumference of the tubular member of the moveable port.

Clause 20. The introducer extension of any one of clauses 17 through 19, wherein the tubular sidewall comprises a flap extending on an exterior surface of the tubular sidewall parallel to the longitudinal axis and extending circumferentially around a portion of the exterior surface from a first edge fixed to the exterior surface, over the slit, to a second free edge.

Clause 21. The introducer extension of any one of clauses 17 through 20, wherein the tubular sidewall comprises a pair of flaps, each extending on an exterior surface of the tubular sidewall parallel to the longitudinal axis and extending circumferentially around a portion of the exterior surface from a first edge fixed to the outer surface to a second free edge at the slit.

Clause 22. A medical assembly comprising: an introducer sheath extending along a longitudinal axis from a distal end of the introducer sheath to a proximal end of the introducer sheath, wherein a distal portion of the sheath is configured to be inserted transdermally into vasculature of a patient; and a hub extending along the longitudinal axis from a distal end of the hub to a proximal end of the hub, wherein a distal end of the hub configured to couple to the proximal end of the introducer sheath; and an introducer extension comprising a tubular sidewall extending along a longitudinal axis from a proximal end of the introducer extension to a distal end of the introducer extension and defining a lumen extending along the longitudinal axis, wherein the distal end of the introducer extension is configured to couple to the proximal end of the hub, and wherein the tubular sidewall is configured to define a curved configuration having at least one curve between the proximal end of the introducer extension and the distal end of the introducer extension, and wherein the introducer sheath, the hub, and the introducer extension define a common lumen configured to allow passage of a medical device therethrough.

Clause 23. The medical assembly of clause 22, comprising a support, the support comprising: a first portion configured to be placed under a patient; and a second portion extending from the first portion and configured to engage an arm of the patient, wherein a body weight of the patient against the first portion stabilizes the second portion to prevent at least one of external abduction or external rotation of the arm of the patient.

Clause 24. The medical assembly of clause 23, wherein the support comprises a rigid plastic support.

Clause 25. The medical assembly of clause 23 or 24, wherein the second portion is configured to position a wrist of the patient near a midsection of the patient.

Clause 26. The medical assembly of any one of clauses 23 through 25, wherein the second portion comprises a retention device configured to, when engaged, limit the mobility of the arm of the patient.

Clause 27. The medical assembly of clause 26, wherein the retention device comprises at least one of a strap, a hook and loop fastener, a button, or a buckle.

Clause 28. The medical assembly of any one of clauses 23 through 27, wherein the hub comprises at least one attachment member configured to engage the support.

Clause 29. A method of forming an introducer extension comprising: forming a tubular sidewall extending along a longitudinal axis from a proximal end of the introducer extension to a distal end of the introducer extension and defining a lumen extending along the longitudinal axis, wherein the tubular sidewall is configured to define a curved configuration having at least one curve between the proximal end and the distal end, wherein the distal end is configured to couple to an introducer sheath, and wherein the lumen is configured to allow passage of a medical device; and shaping the tubular sidewall to define the curved configuration.

Clause 30. The method of clause 29, wherein forming the tubular sidewall comprises: forming an inner layer comprising a first lubricious polymer; and forming, over the inner layer, an outer layer comprising a second polymer.

Clause 31. The method of clause 30, wherein forming the tubular sidewall comprises: forming a coil on a radial outer surface of the inner layer; and forming the outer layer over the inner layer and the coil.

Clause 32. The method of any one of clauses 29 through 31, wherein the tubular sidewall comprises a substantially rigid plastic, and wherein shaping the tubular sidewall comprises thermoforming the tubular sidewall to define a substantially rigid preformed curve.

Clause 33. The method of any one of clauses 29 through 32, wherein forming the tubular sidewall comprises forming an exterior surface of the tubular sidewall such that the tubular sidewall is configured to adjustably bend into the curved configuration.

Clause 34. The method of any one of clauses 29 through 33, wherein forming the tubular sidewall comprises forming the tubular sidewall to expand and contract along the longitudinal axis.

Clause 35. The method of any one of clauses 29 through 34, wherein forming the tubular sidewall comprises forming the tubular sidewall to define a plurality of peaks and troughs, each of the peaks and troughs extending around a circumference of the tubular sidewall transverse to the longitudinal axis, wherein the plurality of peaks and troughs are configured to fold and unfold.

Clause 36. The method of any one of clauses 29 through 35, wherein forming the tubular sidewall comprises forming a plurality of grooves in an exterior surface of tubular sidewall, wherein the plurality of grooves is configured to reduce shear stress in response to bending of the tubular sidewall in at least one direction.

Clause 37. A method of using a medical assembly comprising: introducing a distal portion of an introducer sheath into vasculature of a patient, wherein the introducer sheath extends along a longitudinal axis from the distal end of the introducer sheath to a proximal end of the introducer sheath, and wherein the proximal end of the introducer sheath is coupled to a distal end of a hub extending from the distal end of the hub to a proximal end of the hub; mechanically coupling the proximal end of the hub to a distal end of an introducer extension comprising a tubular sidewall extending along the longitudinal axis from the proximal end of the introducer extension to a distal end of the introducer extension, wherein the tubular sidewall is configured to define a curved configuration having at least one curve between the proximal end of the introducer extension and the distal end of the introducer extension, wherein the introducer sheath, the hub, and the introducer extension define a common lumen; shaping the tubular sidewall into the curved configuration, and introducing a medical device through the common lumen into vasculature of the patient.

Clause 38. The method of clause 37, wherein shaping the tubular sidewall into the curved configuration comprises shaping the tubular sidewall into a first curve extending in a first direction and a second curve extending in a second, different direction.

Clause 39. The method of clause 37 or 38, wherein the tubular sidewall is configured to expand and contract along the longitudinal axis, and wherein shaping the tubular sidewall into the curved configuration comprises expanding the tubular sidewall along the longitudinal axis.

Various examples have been described. Any combination of the described systems, devices, operations, or functions is contemplated. These and other examples are within the scope of the following claims.

What is claimed is:

1. A medical assembly comprising:
    a support configured to position a left wrist of a patient near a midsection of the patient, wherein the support includes a retention device configured to limit mobility of a left arm of the patient to prevent at least one of external abduction or external rotation of the left arm;
    an introducer sheath extending along a longitudinal axis from a distal end of the introducer sheath to a proximal end of the introducer sheath, wherein a distal portion of the introducer sheath is configured to be inserted transdermally into a vasculature of the left arm of the patient;
    a hub extending along the longitudinal axis from a distal end of the hub to a proximal end of the hub, wherein the distal end of the hub is configured to couple to the proximal end of the introducer sheath; and
    an introducer extension comprising:
        a tubular sidewall extending along the longitudinal axis from a proximal end of the introducer extension to a distal end of the introducer extension, wherein the distal end of the introducer extension is configured to couple to the proximal end of the hub, wherein the tubular sidewall is configured to adjustably bend to define a curved configuration having at least one curve between the proximal end of the introducer extension and the distal end of the introducer extension, wherein the tubular sidewall is configured to retain the curved configuration, wherein the tubular sidewall defines a slit extending along the longitudinal axis, and wherein the introducer sheath, the hub, and the introducer extension define a common lumen configured to allow passage of a medical device therethrough; and
        a moveable port configured to move along the tubular sidewall within the slit, wherein the moveable port is configured to travel over the at least one curve when the tubular sidewall retains the curved configuration,
    wherein at least one of the introducer extension or the hub includes an attachment member, the attachment member including a mechanical coupling configured to releasably couple to the retention device of the support,
    wherein the introducer extension defines a length in a range from 5 centimeters to 50 centimeters from the distal end of the introducer extension to the proximal end of the introducer extension, and
    wherein the slit extends over a portion of the length to allow the moveable port to position at a region of the patient containing a femoral access site of a right leg of the patient when the introducer sheath is inserted transdermally into the vasculature of the left arm of the patient, the distal end of the hub is coupled to the proximal end of the introducer sheath, the distal end of the introducer extension is coupled to the proximal end of the hub, and the attachment member is releasably coupled to the retention device.

2. The medical assembly of claim 1, wherein the support comprises:
    a first portion configured to be placed under the patient; and
    a second portion extending from the first portion and configured to engage the left arm of the patient,
    wherein the first portion is configured to stabilize the second portion, to prevent at least one of external abduction or external rotation of the left arm of the patient, while a body weight of the patient is applied to the first portion.

3. The introducer extension of claim 2, wherein the second portion includes the retention device.

4. The medical assembly of claim 1, wherein the support comprises a rigid plastic support.

5. The medical assembly of claim 1, wherein the retention device comprises at least one of a strap, a hook and loop fastener, a button, or a buckle.

6. The medical assembly of claim 1, wherein the hub comprises the attachment member.

7. The medical assembly of claim 1, wherein the at least one curve comprises a first curve extending in a first direction and a second curve extending in a second, different direction.

8. The medical assembly of claim 1, wherein the at least one curve is defined by an arc degree within a range from about 0 degrees to about 90 degrees.

9. The medical assembly of claim 1, wherein the tubular sidewall is configured to expand and contract along the longitudinal axis.

10. The medical assembly of claim 1, wherein the tubular sidewall comprises a substantially rigid plastic.

11. The medical assembly of claim 1, wherein the tubular sidewall defines a plurality of peaks and troughs, each of the peaks and troughs extending around a portion of a circumference of the tubular sidewall substantially transverse to the longitudinal axis.

12. The medical assembly of claim 11, wherein the plurality of peaks and troughs are configured to fold and unfold to at least one of expand and contract the tubular sidewall along the longitudinal axis or adjustably bend into the curved configuration.

13. The medical assembly of claim 1, wherein an exterior surface of the tubular sidewall defines a plurality of grooves, wherein the plurality of grooves is configured to reduce shear stress in response to bending of the tubular sidewall in at least one direction.

14. The medical assembly of claim 1, wherein the tubular sidewall comprises a plurality of layers.

15. The medical assembly of claim 14, wherein the plurality of layers comprises:
an inner layer comprising a first, lubricious polymer; and
an outer layer comprising a second, different polymer.

16. The medical assembly of claim 15, wherein the inner layer comprises at least one of polytetrafluoroethylene or high-density polyethylene, and wherein the outer layer comprises at least one of a polyamide or a polyether block amide.

17. The medical assembly of claim 1, wherein the length of the introducer extension is configured to extend from the left wrist of the patient to the midsection of the patient.

18. The medical assembly of claim 1, wherein the introducer extension is configured to extend from the left wrist of the patient to the midsection of the patient with a proximal end of the common lumen oriented toward a left side of the patient.

19. The medical assembly of claim 1, wherein the moveable port comprises:
an annular body having an outer surface and an inner surface, each extending from a proximal face to a distal face, wherein the outer surface is configured to be manipulated by a clinician, and wherein the inner surface is configured to at least partially surround the tubular sidewall in sliding engagement; and
a tubular member extending from a proximal end at a first aperture defined by the outer surface to a distal end, wherein the tubular member extends through the slit such that a member lumen of the tubular member is fluidly coupled to the common lumen, wherein the moveable port is moveable along the tubular sidewall to adjust a longitudinal position of the tubular member.

20. The introducer extension of claim 19, wherein the member lumen of the tubular member at the distal end is substantially parallel to the longitudinal axis, wherein the member lumen of the tubular member at the proximal end of the tubular member is substantially perpendicular to the longitudinal axis.

21. The introducer extension of claim 19, wherein the tubular sidewall comprises a resilient material configured to deform around a circumference of the tubular member of the moveable port.

22. The introducer extension of claim 19, wherein the tubular sidewall comprises a flap extending on an exterior surface of the tubular sidewall parallel to the longitudinal axis and extending circumferentially around a portion of the exterior surface from a first edge fixed to the exterior surface, over the slit, to a second free edge, wherein the second free edge is configured to deform around the tubular member when the moveable port slides along the tubular sidewall.

23. The introducer extension of claim 19, wherein the tubular sidewall comprises a pair of flaps, each extending on an exterior surface of the tubular sidewall parallel to the longitudinal axis and extending circumferentially around a portion of the exterior surface from a first edge fixed to the outer surface to a second free edge at the slit.

24. A method of forming a medical assembly, the method comprising:
forming a tubular sidewall extending along a longitudinal axis from a proximal end of an introducer extension to a distal end of the introducer extension and defining a sidewall lumen extending along the longitudinal axis, wherein the tubular sidewall is configured to adjustably bend to define a curved configuration having at least one curve between the proximal end and the distal end, wherein the tubular sidewall is configured to retain the curved configuration, wherein the tubular sidewall defines a slit extending along the longitudinal axis, wherein the distal end is configured to couple to a proximal end of a hub, the hub being configured to couple to a proximal end of an introducer sheath, and wherein the lumen is configured to allow passage of a medical device, wherein the introducer extension defines a length in a range from 5 centimeters to 50 centimeters from the distal end of the introducer extension to the proximal end of the introducer extension;
disposing a moveable port within the slit defined by the tubular sidewall, wherein the movable port is configured to travel over the at least one curve when the tubular sidewall retains the curved configuration, wherein the slit extends over a portion of the length to allow the moveable port to position at a region containing a femoral access site of a right leg of a patient when the introducer sheath is inserted transdermally into a vasculature of a left arm of the patient when the hub is coupled to the introducer extension and the proximal end of the introducer sheath;
defining, using the introducer extension, the introducer sheath, and the hub, a common lumen configured to allow passage of the medical device therethrough, wherein the introducer sheath extends along the longitudinal axis from a distal end of the introducer sheath to a proximal end of the introducer sheath, wherein a distal portion of the introducer sheath is configured to be inserted transdermally into vasculature of the patient, and wherein the hub extends along the longitudinal axis from a distal end of the hub to the proximal end of the hub, wherein the distal end of the hub is configured to couple to the proximal end of the introducer sheath;
forming a retention device on a support; and
forming an attachment member on at least one of the introducer extension or the hub, wherein the attachment member includes a mechanical coupling configured to releasably couple to the retention device, wherein the support is configured to position a left wrist of the patient near a midsection of the patient, and wherein the retention device is configured to limit the mobility of the left arm of the patient to prevent at least one of external abduction or external rotation of the left arm, wherein the slit is configured to position the moveable port at the region of the patient containing the femoral access site of the right leg of the patient when the introducer sheath is inserted transdermally into the vasculature of the left arm of the patient, the distal end of the hub is coupled to the introducer sheath, and the distal end of the introducer extension is coupled to the proximal end of the hub, wherein the introducer extension defines a length from the distal end of the introducer extension to the proximal end of the introducer extension, and wherein the slit extends over a portion of the length.

25. The method of claim 24, wherein forming the tubular sidewall comprises:
    forming an inner layer comprising a first lubricious polymer; and
    forming, over the inner layer, an outer layer comprising a second polymer.

26. The method of claim 24, wherein the tubular sidewall comprises a substantially rigid plastic, and wherein forming the tubular sidewall comprises thermoforming the tubular sidewall to define a substantially rigid preformed curve.

27. The method of claim 24, wherein forming the tubular sidewall comprises forming an exterior surface of the tubular sidewall such that the tubular sidewall is configured to adjustably bend into the curved configuration.

28. The method of claim 24, wherein forming the tubular sidewall comprises forming the tubular sidewall to expand and contract along the longitudinal axis.

29. The method of claim 24, wherein forming the tubular sidewall comprises forming the tubular sidewall to define a plurality of peaks and troughs, each of the peaks and troughs extending around a portion of a circumference of the tubular sidewall transverse to the longitudinal axis, wherein the plurality of peaks and troughs are configured to fold and unfold.

30. The method of claim 24, wherein forming the tubular sidewall comprises forming a plurality of grooves in an exterior surface of tubular sidewall, wherein the plurality of grooves is configured to reduce shear stress in response to bending of the tubular sidewall in at least one direction.

31. A method of using a medical assembly, the method comprising:
    positioning, using a support, a left wrist of a patient near a midsection of the patient, wherein the support includes a retention device configured to limit the mobility of a left arm of the patient to prevent at least one of external abduction or external rotation of the left arm;
    introducing a distal portion of an introducer sheath into a vasculature of the left arm of the patient, wherein the introducer sheath extends along a longitudinal axis from a distal end of the introducer sheath to a proximal end of the introducer sheath, and wherein the proximal end of the introducer sheath is coupled to a distal end of a hub, and wherein the hub extends from the distal end of the hub to a proximal end of the hub;
    mechanically coupling the proximal end of the hub to a distal end of an introducer extension comprising a tubular sidewall extending along the longitudinal axis from a proximal end of the introducer extension to the distal end of the introducer extension, wherein the tubular sidewall is configured to adjustably bend to define a curved configuration having at least one curve between the proximal end of the introducer extension and the distal end of the introducer extension, wherein the tubular sidewall is configured to retain the curved configuration, wherein the tubular sidewall defines a slit extending along the longitudinal axis and wherein the introducer extension comprises a movable port disposed within the slit, wherein the movable port is configured to travel over the at least one curve when the tubular sidewall retains the curved configuration, and wherein the introducer sheath, the hub, and the introducer extension define a common lumen;
    shaping the tubular sidewall into the curved configuration;
    releasably coupling, using a mechanical coupling of an attachment member, the retention device of the support to at least one of the introducer extension or the hub, wherein the at least one of the introducer extension or the hub includes the attachment member;
    positioning, using the slit, the moveable port at a region of the patient containing a femoral access site of a right leg of the patient when the introducer sheath is inserted transdermally into the vasculature of the left arm of the patient, the distal end of the hub is coupled to the proximal end of the introducer sheath, and the distal end of the introducer extension is coupled to the proximal end of the hub, wherein the introducer extension defines a length in a range from 5 centimeters to 50 centimeters from the distal end of the introducer extension to the proximal end of the introducer extension, and wherein the slit extends over a portion of the length; and
    introducing a medical device through the common lumen into vasculature of the patient.

32. The method of claim 31, wherein shaping the tubular sidewall into the curved configuration comprises shaping the tubular sidewall into a first curve extending in a first direction and a second curve extending in a second, different direction.

33. The method of claim 31, wherein the tubular sidewall is configured to expand and contract along the longitudinal axis, and wherein shaping the tubular sidewall into the curved configuration comprises expanding the tubular sidewall along the longitudinal axis.

34. The method of claim 31,
    wherein the moveable port comprises:
        an annular body having an outer surface and an inner surface, each extending from a proximal face to a distal face, wherein the outer surface is configured to be manipulated by a clinician, and wherein the inner surface is configured to at least partially surround the tubular sidewall in sliding engagement; and
        a tubular member extending from a proximal end at a first aperture defined by the outer surface to a distal end, wherein the tubular member extends through the slit such that a member lumen of the tubular member is fluidly coupled to a sidewall lumen of the tubular sidewall,
    wherein the moveable port is moveable along the tubular sidewall to adjust a longitudinal position of the tubular member, and
    wherein the method further comprises moving the moveable port along the tubular sidewall to a target position.

* * * * *